(12) United States Patent
Shuber

(10) Patent No.: US 6,964,846 B1
(45) Date of Patent: Nov. 15, 2005

(54) METHODS FOR DETECTING NUCLEIC ACIDS INDICATIVE OF CANCER

(75) Inventor: Anthony P. Shuber, Milford, MA (US)

(73) Assignee: Exact Sciences Corporation, Maynard, MA (US)

( * ) Notice: Subject to any disclaimer, the term of this patent is extended or adjusted under 35 U.S.C. 154(b) by 0 days.

(21) Appl. No.: 09/545,162

(22) Filed: Apr. 7, 2000

Related U.S. Application Data

(60) Provisional application No. 60/128,629, filed on Apr. 9, 1999.

(51) Int. Cl.[7] .............................. C12P 19/34; C12Q 1/68
(52) U.S. Cl. ............................................ 435/6; 435/91.2
(58) Field of Search .................... 435/6, 91.2; 536/23.1

(56) References Cited

U.S. PATENT DOCUMENTS

| | | | |
|---|---|---|---|
| 3,413,464 A | 11/1968 | Kamentsky | |
| 4,101,279 A | 7/1978 | Aslam | |
| 4,309,782 A | 1/1982 | Paulin | |
| 4,333,734 A | 6/1982 | Fleisher | |
| 4,358,535 A | 11/1982 | Falkow et al. | |
| 4,445,235 A | 5/1984 | Slover et al. | |
| 4,535,058 A | 8/1985 | Weinberg et al. | |
| 4,578,358 A | 3/1986 | Oksman et al. | |
| 4,683,195 A | 7/1987 | Mullis et al. | |
| 4,683,202 A | 7/1987 | Mullis | |
| 4,705,050 A | 11/1987 | Markham | |
| 4,735,905 A | 4/1988 | Parker | |
| 4,786,718 A | 11/1988 | Weinberg et al. | |
| 4,857,300 A | 8/1989 | Maksem | |
| 4,871,838 A | 10/1989 | Bos et al. | |
| 4,935,342 A | 6/1990 | Seligson et al. | |
| 4,981,783 A | 1/1991 | Augenlicht | |
| 4,982,615 A | 1/1991 | Sultan et al. | |
| 5,087,617 A | 2/1992 | Smith | |
| 5,126,239 A | 6/1992 | Livak et al. | |
| 5,137,806 A | 8/1992 | LeMaistre et al. | |
| 5,149,506 A | 9/1992 | Skiba et al. | |
| 5,196,167 A | 3/1993 | Guadagno et al. | |
| 5,200,314 A | 4/1993 | Urdea | |
| 5,248,671 A | 9/1993 | Smith | |
| 5,272,057 A | 12/1993 | Smulson et al. | |
| 5,302,509 A | 4/1994 | Cheeseman | |
| 5,330,892 A | 7/1994 | Vogelstein et al. | |
| 5,331,973 A | 7/1994 | Fiedler et al. | |
| 5,348,855 A | 9/1994 | Dattagupta et al. | |
| 5,352,775 A | 10/1994 | Albertsen et al. | |
| 5,362,623 A | 11/1994 | Vogelstein et al. | |

(Continued)

FOREIGN PATENT DOCUMENTS

| AU | A-11325/95 | 10/1994 |
|---|---|---|
| AU | 711754 | 7/1997 |

(Continued)

OTHER PUBLICATIONS

Ditkoff et al. Surgery, 1996, vol. 120, No. 6, 959–965.*
Smith–Ravin et al. Gut 1995, 36:81–86.*

(Continued)

*Primary Examiner*—Juliet C. Switzer
(74) *Attorney, Agent, or Firm*—Mintz, Levin, Cohn, Ferris, Glovsky and Popeo, P.C.; Ivor R. Elrifi

(57) ABSTRACT

The invention provides methods for screening tissue or body fluid samples for nucleic acid indicia of cancer or precancer.

Method are provided for screening a patient for cancer or precancer by detecting the presence of nucleic acid fragments that are longer than nucleic acid fragments expected to be present in a sample obtained from a healthy individual. In one embodiment, a positive screen for cancer or precancer is identified when a patient tissue or body fluid sample comprising exfoliated cells or cellular debris contains an amount of nucleic acid of a length greater than about 200 base pairs that exceeds a predetermined amount.

5 Claims, 11 Drawing Sheets

U.S. PATENT DOCUMENTS

| | | |
|---|---|---|
| 5,369,004 A | 11/1994 | Polymeropoulos et al. |
| 5,378,602 A | 1/1995 | Polymeropoulos et al. |
| 5,380,645 A | 1/1995 | Vogelstein |
| 5,380,647 A | 1/1995 | Bahar |
| 5,382,510 A | 1/1995 | Levine et al. |
| 5,409,586 A | 4/1995 | Kamahori et al. |
| 5,416,025 A | 5/1995 | Krepinsky et al. |
| 5,458,761 A | 10/1995 | Kamahori et al. |
| 5,463,782 A | 11/1995 | Carlson et al. |
| 5,466,576 A | 11/1995 | Schulz et al. |
| 5,468,610 A | 11/1995 | Polymeropoulos et al. |
| 5,468,613 A | 11/1995 | Erlich et al. |
| 5,482,834 A | 1/1996 | Gillespie |
| 5,489,508 A | 2/1996 | West et al. |
| 5,492,808 A | 2/1996 | de la Chapelle et al. |
| 5,496,470 A | 3/1996 | Lenhart |
| 5,506,105 A | 4/1996 | Haydock |
| 5,508,164 A | 4/1996 | Kausch et al. |
| 5,512,441 A | 4/1996 | Ronai |
| 5,514,547 A | 5/1996 | Balazs et al. |
| 5,527,676 A | 6/1996 | Vogelstein et al. |
| 5,532,108 A | 7/1996 | Vogelstein |
| 5,538,851 A | 7/1996 | Fach et al. |
| 5,559,014 A | 9/1996 | Estes et al. |
| 5,580,729 A | 12/1996 | Vogelstein |
| 5,589,335 A | 12/1996 | Kearney et al. |
| 5,599,662 A | 2/1997 | Respess |
| 5,612,473 A | 3/1997 | Wu et al. |
| 5,635,352 A | 6/1997 | Urdea et al. |
| 5,641,628 A | 6/1997 | Bianchi |
| 5,645,995 A * | 7/1997 | Kieback ..................... 435/6 |
| 5,670,325 A | 9/1997 | Lapidus et al. |
| 5,688,643 A | 11/1997 | Oka et al. |
| 5,709,998 A | 1/1998 | Kinzler et al. |
| 5,710,028 A | 1/1998 | Eyal et al. |
| 5,741,650 A | 4/1998 | Lapidus et al. |
| 5,759,777 A | 6/1998 | Kearney et al. |
| 5,830,665 A | 11/1998 | Shuber et al. |
| 5,846,710 A | 12/1998 | Bajaj |
| 5,856,104 A | 1/1999 | Chee et al. |
| 5,882,865 A | 3/1999 | Vogelstein et al. |
| 5,888,778 A | 3/1999 | Shuber |
| 5,910,407 A | 6/1999 | Vogelstein et al. |
| 5,916,744 A | 6/1999 | Taylor |
| 5,928,870 A | 7/1999 | Lapidus et al. |
| 5,942,396 A * | 8/1999 | Shiff et al. ..................... 435/6 |
| 5,952,178 A | 9/1999 | Lapidus et al. |
| 5,976,800 A | 11/1999 | Lau et al. |
| 6,020,137 A | 2/2000 | Lapidus et al. |
| 6,037,465 A | 3/2000 | Hillebrand et al. |
| 6,084,091 A | 7/2000 | Muller et al. |
| 6,100,029 A | 8/2000 | Lapidus et al. |
| 6,143,529 A * | 11/2000 | Lapidus et al. .......... 435/91.2 |
| 6,146,828 A | 11/2000 | Lapidus |
| 6,150,100 A | 11/2000 | Ruschoff et al. |
| 6,177,251 B1 | 1/2001 | Vogelstein et al. |
| 6,203,993 B1 | 3/2001 | Shuber et al. |
| 6,214,187 B1 | 4/2001 | Hammond et al. |
| 6,214,558 B1 | 4/2001 | Shuber et al. |
| 6,228,596 B1 | 5/2001 | Macina et al. ................. 435/6 |
| 6,238,927 B1 | 5/2001 | Abrams et al. |
| 6,251,660 B1 | 6/2001 | Muir et al. |
| 6,268,136 B1 | 7/2001 | Shuber et al. |
| 6,280,947 B1 | 8/2001 | Shuber et al. |
| 6,300,077 B1 | 10/2001 | Shuber et al. |
| 6,303,304 B1 | 10/2001 | Shuber et al. |
| 6,351,857 B2 | 3/2002 | Slaon, III et al. |
| 6,406,857 B1 | 6/2002 | Shuber et al. |
| 6,415,455 B1 | 7/2002 | Slaon, III et al. |
| 6,428,964 B1 | 8/2002 | Shuber |
| 6,448,002 B1 | 9/2002 | Hillebrand et al. |
| 6,475,738 B2 | 11/2002 | Shuber et al. |
| 6,482,595 B2 | 11/2002 | Shuber et al. |
| 6,498,012 B2 | 12/2002 | Laken |
| 6,503,718 B2 | 1/2003 | Shuber et al. |
| 6,551,777 B1 | 4/2003 | Shuber et al. |
| 6,586,177 B1 | 7/2003 | Shuber ..................... 435/6 |
| 2001/0018180 A1 | 8/2001 | Shuber et al. |
| 2001/0039012 A1 | 11/2001 | Lapidus ..................... 435/6 |
| 2001/0042264 A1 | 11/2001 | Sloan et al. ................. 4/315 |
| 2002/0001800 A1 | 1/2002 | Lapidus ..................... 435/6 |
| 2002/0004201 A1 | 1/2002 | Lapidus et al. ............. 435/6 |
| 2002/0025525 A1 | 2/2002 | Shuber |
| 2002/0040498 A1 | 4/2002 | Sloan et al. ................. 4/315 |
| 2002/0045183 A1 | 4/2002 | Shuber et al. .............. 435/6 |
| 2002/0048752 A1 | 4/2002 | Lapidus et al. ............. 435/6 |
| 2002/0064787 A1 | 5/2002 | Shuber et al. .............. 435/6 |
| 2002/0110810 A1 | 8/2002 | Shuber |
| 2002/0119469 A1 | 8/2002 | Shuber et al. |
| 2002/0119472 A1 | 8/2002 | Lapidus et al. |
| 2002/0123052 A1 | 9/2002 | Laken ..................... 435/6 |
| 2002/0132251 A1 | 9/2002 | Shuber |
| 2002/0164631 A1 | 11/2002 | Shuber et al. |
| 2003/0044780 A1 | 3/2003 | Lapidus et al. |
| 2003/0049659 A1 | 3/2003 | Lapidus et al. |
| 2003/0087258 A1 | 5/2003 | Shuber |

FOREIGN PATENT DOCUMENTS

| | | |
|---|---|---|
| AU | 704696 | 8/1997 |
| AU | 745862 | 9/1998 |
| AU | 744746 | 1/1999 |
| AU | 720489 | 9/1999 |
| AU | AU199942333 A1 | 9/1999 |
| CA | 2228769 | 2/1997 |
| CA | 2211702 | 5/1999 |
| DE | 195 30 132 C2 | 2/1997 |
| DE | 195 30 132 A1 | 2/1997 |
| DE | 197 12 332 A1 | 10/1998 |
| DE | 197 36 691 A1 | 2/1999 |
| EP | 0 270 017 A3 | 6/1988 |
| EP | 0 270 017 A2 | 6/1988 |
| EP | 0 284 362 A2 | 9/1988 |
| EP | 0 284 362 A3 | 9/1988 |
| EP | 0 337 498 A2 | 10/1989 |
| EP | 0 390 323 A2 | 10/1990 |
| EP | 0 390 323 A3 | 10/1990 |
| EP | 0 391 565 B1 | 10/1990 |
| EP | 0 407 789 B1 | 1/1991 |
| EP | 0 407 789 A1 | 1/1991 |
| EP | 0 608 004 A2 | 7/1994 |
| EP | 0 259 031 B1 | 11/1994 |
| EP | 0 648 845 A2 | 4/1995 |
| EP | 0 664 339 A1 | 7/1995 |
| GB | 2327497 A | 1/1999 |
| JP | 3325270 | 9/2002 |
| WO | WO 90/09455 | 8/1990 |
| WO | WO 92/13103 | 8/1992 |
| WO | WO 92/16657 | 10/1992 |
| WO | WO 93/18186 | 9/1993 |
| WO | WO 93/20233 | 10/1993 |
| WO | WO 93/20235 | 10/1993 |
| WO | WO 94/00603 | 1/1994 |
| WO | WO 94/01447 | 1/1994 |
| WO | WO 94/09161 | 4/1994 |
| WO | WO 94/10575 | 5/1994 |
| WO | WO 94/11383 | 5/1994 |
| WO | WO 95/00669 | 1/1995 |
| WO | WO 95/07361 | 3/1995 |
| WO | WO 95/09928 | 4/1995 |
| WO | WO 95/09929 | 4/1995 |
| WO | WO 95/12606 | 5/1995 |

| | | |
|---|---|---|
| WO | WO 95/13397 | 5/1995 |
| WO | WO 95/15400 | 6/1995 |
| WO | WO 95/16792 | 6/1995 |
| WO | WO 95/18818 | 7/1995 |
| WO | WO 95/19448 | 7/1995 |
| WO | WO 95/25813 | 9/1995 |
| WO | WO 95/31728 | 11/1995 |
| WO | WO 96/01907 | 1/1996 |
| WO | WO 96/06951 | 3/1996 |
| WO | WO 96/08514 | 3/1996 |
| WO | WO 96/12821 | 5/1996 |
| WO | WO 96/13611 | 5/1996 |
| WO | WO 96/23895 A | 8/1996 |
| WO | WO 96/29430 A | 9/1996 |
| WO | WO 96/30545 | 10/1996 |
| WO | WO 97/07239 | 2/1997 |
| WO | WO 97/09449 | 3/1997 |
| WO | WO 97/09600 | 3/1997 |
| WO | WO 97/19191 A | 5/1997 |
| WO | WO 97/23651 | 7/1997 |
| WO | WO 97/25442 | 7/1997 |
| WO | WO 97/28450 | 8/1997 |
| WO | WO 98/08971 | 3/1998 |
| WO | WO 98/38338 | 9/1998 |
| WO | WO 98/39478 | 9/1998 |
| WO | WO 98/58081 | 12/1998 |
| WO | WO 98/58084 | 12/1998 |
| WO | WO 99/07894 | 2/1999 |
| WO | WO 99/07895 | 2/1999 |
| WO | WO 99/10528 | 3/1999 |
| WO | WO 99/20798 | 4/1999 |
| WO | WO 99/26724 | 6/1999 |
| WO | WO 99/28507 | 6/1999 |
| WO | WO 99/45147 | 9/1999 |
| WO | WO 99/45374 | 9/1999 |
| WO | WO 99/53316 | 10/1999 |
| WO | WO 99/55912 | 11/1999 |
| WO | WO 99/60160 | 11/1999 |
| WO | WO 99/60161 | 11/1999 |
| WO | WO 99/60162 | 11/1999 |
| WO | WO 99/66077 | 12/1999 |
| WO | WO 99/66078 | 12/1999 |
| WO | WO 99/66079 | 12/1999 |
| WO | WO 00/09751 | 2/2000 |
| WO | WO 00/11215 | 3/2000 |
| WO | WO 00/31298 | 6/2000 |
| WO | WO 00/31305 | 6/2000 |
| WO | WO 00/31313 | 6/2000 |
| WO | WO 00/32820 | 6/2000 |
| WO | WO 00/50640 | 8/2000 |
| WO | WO 00/50870 | 8/2000 |
| WO | WO 00/58514 A3 | 10/2000 |
| WO | WO 00/60118 | 10/2000 |
| WO | WO 00/61808 A3 | 10/2000 |
| WO | WO 00/66005 | 11/2000 |
| WO | WO 00/70096 | 11/2000 |
| WO | WO 00/70096 A3 | 11/2000 |
| WO | WO01/11083 A2 | 2/2001 |
| WO | WO01/11083 A3 | 2/2001 |
| WO | WO 01/18252 A2 | 3/2001 |
| WO | WO 01/42502 A2 | 6/2001 |
| WO | WO 01/42503 A2 | 6/2001 |
| WO | WO 01/42781 A2 | 6/2001 |
| WO | WO01/64950 A3 | 9/2001 |
| WO | WO01/64950 A2 | 9/2001 |
| WO | WO02/055740 A2 | 7/2002 |
| WO | WO02/059379 A2 | 8/2002 |
| WO | WO02/074995 A1 | 9/2002 |
| WO | WO02/092858 A2 | 11/2002 |
| WO | WO 03/044217 | 5/2003 |
| WO | WO 03/071252 | 8/2003 |

OTHER PUBLICATIONS

Aaltonen et al. (1994) "Replication Errors in Benign and Malignant Tumors from Hereditary Nonpolyposis Colorectal Cancer Patients" *Cancer Research* 54:1645–1648.

Aaltonen et al. (1998) "Incidence of Hereditary Nonpolyposis Colorectal Cancer and the Feasibility of Molecular Screening for the Disease" *The New England Journal of Medicine* 338:1481–1487.

Ausubel et al., (1995), *Short Protocols in Molecular Biology*, 3d ed., pp. 2–3–2–12, 3–30–3–33.

Bertario et al. (1999) "Risk of Colorectal Cancer Following Colonoscopic Polypectomy" *Tumori* 85:157–162.

Beskin et al., (1995), "On the Mechanism of the Modular Primer Effect," *Nucleic Acids Research*, vol. 23, No. 15, 2881–2885.

Blum H.E., (1995) "Colorectal Cancer: Future Population Screening for Early Colorectal Cancer" *European Journal of Cancer*, vol. 31A, pp. 1369–1372.

Bos et al., (May 28, 1987) "Prevalence of ras Gene Mutations in Human Colorectal Cancers," *Nature*, vol. 327, pp. 293–297.

Caldas et al., (Jul. 1, 1994) "Detection of K–ras Mutations in the Stool of Patients with Pancreatic Adenocarcinoma and Pancreatic Ductal Hyperplasia" *Cancer Research*, vol. 54, pp. 3568–3573.

Capozzi et al. (1999) "Evaluation of the Replication Error Phenotype in Relation to Molecular and Clinicopathological Features in Hereditary and Early Onset Colorectal Cancer" *European Journal of Cancer* 35: 289–295.

Cave et al., (1994) "Reliability of PCR Directly from Stool Samples: Usefulness of an Internal Standard," *BioTechniques*, vol. 16, No. 5, pp. 809–810.

Chapelle (1999) "Testing Tumors for Microsatellite Instability" *European Journal of Human Genetics* 7:407–408.

Charlesworth et al., (Sep. 15, 1994) "The Evolutionary Dynamics of Repetitive DNA in Eukaryotes," *Nature*, vol. 371, pp. 215–220.

Chen et al. (1997) "Microsatellite Instability in Sporadic-Colon–Cancer Patients With and Without Liver Metastases" *International Journal of Cancer* 74:470–474.

Coll et al., (Oct. 1989) "Evaluation of a Rapid Method of Extracting DNA from Stool Samples for Use in Hybridization Assays," *Journal of Clinical Microbiology*, vol. 27, No. 10, pp. 2245–2248.

Coughlin et al. (1999) "Public Health Perspectives on Testing for Colorectal Cancer Susceptibility Genes" *American Journal of Preventive Medicine* 16:99–104.

Cunningham C. and M.G. Dunlop, (1996) "Molecular Genetic Basis of Colorectal Cancer Susceptibility," *British Journal of Surgery*, vol. 83, pp. 321–329.

Deng et al., (Dec. 20, 1996) "Loss of Heterozygosity in Normal Tissue Adjacent to Breast Carcinomas," *Science*, vol. 274, pp. 2057–2059.

Deuter et al., (1995) "A Method for Preparation of Fecal DNA Suitable for PCR," *Nucleic Acids Research*, vol. 23, No. 18, pp. 3800–3801.

Dib et al., (Mar. 14, 1996) "A Comprehensive Genetic Map of the Human Genome Based on 5,264 Microsatellites," *Nature* vol. 380, pp. 152–154.

Duffy M.J., (1995) "Can Molecular Markers Now be Used for Early Diagnosis of Malignancy?" *Clin. Chem,.* vol. 41, No. 10, pp. 1410–1413.

Eguchi et al., (Apr. 15, 1996) "Mutations of the p53 Gene in the Stool of Patients with Resectable Colorectal Cancer," *Cancer Supplement*, vol. 77, No. 8, pp. 1707–1710.

Enari et al., (Jan. 1, 1998) "A Caspase–Activated DNase that Degrades DNA During Apoptosis, and its Inhibitor ICAD," *Nature*, vol. 391, pp. 43–50.

Fearon, E.R., (1995) "16 Molecular Abnormalities in Colon and Rectal Cancer," *The Molecular Basis of Cancer*, pp. 340–357.

Grossman et al. (1988), "Colonoscopic Screening of persons With Suspected Risk Factors for Colon Cancer" *Gastroenterology* 94:395–400.

Gyllensten U. B., Allen M., (1995) "Sequencing of In Vitro Amplified DNA," *Recombinant DNA Methodology II*, (Wu, ed.), pp. 565–578.

Hasegawa et al., (1995) "Detection of K–ras Mutations in DNAs Isolated From Feces of Patients with Colorectal Tumors by Mutant–Allele–Specific Amplification (MASA)," *Oncogene*, vol. 10, pp. 1441–1445.

Hoang et al. (1997) "BAT–26, an Indicator of the Replication Error Phenotype in Cancers and Colorectal Cell Lines" *Cancer Research* 57:300–303.

Honchel et al., (1995) "Genomic Instability in Neoplasia," *Seminars in Cell Biology*, vol. 6, pp. 45–52.

Hoss et al., (Sep. 17, 1992) "Excrement Analysis by PCR" *Scientific Correspondence* pp. 199.

Iino et al. (1999) "DNA Microsatellite Instability in Hyperplastic Polyps, Serrated Adenomas, and Mixed Polyps: a Mild Mutator Pathway for Colorectal Cancer?" *Journal of Clinical Pathology* 52:5–9.

Iniesta et al. (1998) "Genetic Abnormalities and Microsatellite Instability in Colorectal Cancer" *Cancer Detection and Prevention* 22:383–395.

Ishimaru et al. (1995) "Microsatellite Instability in Primary and Metastatic Colorectal Cancers" *International Journal of Cancer* 64:153–157.

Jarvinen et al. (1995) "Screening Reduces Colorectal Cancer Rate in Families With Hereditary Nonpolyposis Colorectal Cancer" *Gastroenterology* 108:1405–1411.

Jernvall et al. (1999) "Microsatellite Instability: Impact on Cancer Progression in Proximal and Distal Colorectal Cancers" *European Journal of Cancer* 35:197–201.

Jessup J.M. and G.E. Gallick, (Sep./Oct. 1992) "The Biology of Colorectal Carcinoma," *Current Problems in Cancer*, pp. 263–328.

Jonsson et al., (Jan. 1995) "From Mutation Mapping to Phenotype Cloning," *Proc. Natl. Acad. Sci.*, vol. 92, pp. 83–85.

Kim et al. (1998) "Microsatellite Instability in Young Patients With Colorectal Cancer" *Pathology International* 48:586–594.

Konishi et al. (1996) "Molecular Nature of Colon Tumors in Hereditary Nonpolyposis Colon Cancer, Familial Polyposis, and Sporadic Colon Cancer" *Gastroenterology* 111:307–317.

Lamberti et al. (1999) "Microsatellite Instability—a Useful Diagnostic Tool to Select Patients at High Risk for Hereditary Non–Polyposis Colorectal Cancer: A Study in Different Groups of Patients With Colorectal Cancer" *Gut* 44:839–843.

Lengauer et al., (Dec. 17, 1998) "Genetic Instabilities in Human Cancers," *Nature*, vol. 396, pp. 643–649.

Leong et al., (1993) "Detection of MYCN Gene Amplification and Deletions of Chromosome 1p in Neuroblastoma by In Situ Hybridization Using Routine Histologic Sections," *Laboratory Investigations*, vol. 69, No. 1, pp. 43–50.

Lin et al. (1998) "Colorectal and Extracolonic Cancer Variations in MHL1/MSH2 Hereditary Nonpolyposis Colorectal Cancer Kindreds and the General Population" *Diseases of the Colon & Rectum* 41:428–433.

Litia et al., (1992) "Simultaneous Detection of Two Cystic Fibrosis Alleles Using Dual–Label Time–Resolved Fluorometry," *Molecular and Cellular Probes*, vol. 6, pp. 505–512.

Lieonart et al. (1998) "Microsatellite Instability and p53 Mutations in Sporadic Right and Left Colon Carcinoma" *American Cancer Society* 83:889–895.

Loktionov A. and I. K. O'Neill, (1995) "Early Detection of Cancer–Associated Gene Alternations in DNA Isolated from Rat Feces During Intestinal Tumor Induction with 1,2–Dimethylhydrazine," *International Journal of Oncology*, vol. 6, pp. 437–445.

Loktionov et al., (Feb., 1998) "Quantitation of DNA from Exfoliated Colonocytes Isolated from Human Stool Surface as a Novel Noninvasive Screening Test for Colorectal Cancer," *Clinical Cancer Research*, vol. 4, pp. 337–341.

Mao L. et al., (Feb. 2, 1996) "Molecular Detection of Primary Bladder Cancer by Microsatellite Analysis," *Science*, vol. 271, pp. 659–662.

Myers, R.M., (Feb. 12, 1993) "The Pluses of Subtraction," *Science*, vol. 259, pp. 942–943.

Naber S. P., (Dec. 1, 1994) "Molecular Pathology—Detection of Neoplasia," *New England Journal of Medicine*, vol. 331, No. 22, pp. 1508–1510.

Nollau et al., (May 1996) "Isolation of DNA from Stool and Bodily Fluids for PCR Amplification," *BioTechniques*, vol. 20, No. 5, pp. 784–788.

Nollau et al., (1996) "Detection of K–ras Mutations in Stools of Patients with Colorectal Cancer by Mutant–Enriched PCR," *Int. J. Cancer*, vol. 66, pp. 332–336.

Orlow I., et al., (Oct. 18, 1995) "Detection of the p16 and p15 Genes in Human Bladder Tumors *Journal of the National Cancer Institute*," vol. 87, No. 20, pp. 1524–1529.

Orou et al., (1995) "Allele–Specific Competitive Blocker PCR: A One–Step Method With Applicability to Pool Screening" *Human Mutation* vol. 6, 163–169.

Park et al. (1999) "Gene–Environment Interaction in Hereditary Nonpolyposis Colorectal Cancer with Implications for Diagnosis and Genetic Testing" *International Journal of Cancer* 82:516–519.

Peltomaki et al. (1997) "Mutations Predisposing to Hereditary Nonpolyposis Colorectal Cancer: Database and Results of a Collaborative Study" *Gastroenterology* 113:1146–1158.

Pharmacia, (1999) *BioDirectory*, pp. 104–109.

Pharmacia, (1991/1992) *Molecular and Cell Biology Catalogue*, pp. 8.3–8.6.

Piao et al., (Sep. 1997) "Relationship between Loss of Heterozygosity of Tumor Suppressor Genes and Histologic Differentiation in Hepatocellular Carcinoma," *Cancer*, vol. 80, No. 5, pp. 865–872.

Ponz de Leon et al. (1998) "Frequency and Type of Colorectal Tumors in Asymtomatic High–Risk Individuals in Families with Hereditary Nonpolyposis Colorectal Cancer" *Cancer Epidemiology, Biomarkers & Prevention* 7:639–641.

Ponz de Leon et al. (1999) "Hereditary Colorectal Cancer in the General Population: From Cancer Registration to Molecular Diagnosis" *Gut* 45:32–38.

Pyatt et al. (1999) "Polymorphic Variation at the BAT–25 and BAT–26 Loci in Individuals of African Origin" *American Journal of Pathology* 155:349–353.

Raff, M., (Nov. 12, 1998) "Cell Suicide for Beginners," *Nature*, vol. 396, pp. 119–122.

Rashid et al. (1999) "Genetic Epidemiology of Mutated K–*ras* Proto–Oncogene, Altered Suppressor Genes, and Microsatellite Instability in Colorectal Adenomas" *Gut* 44:826–833.

Ravelingien et al., (1995) "Contribution of Molecular Oncology in the Detection of Colorectal Carcinomas," *Acta Gastro–Enterologica Belgica*, vol. 58, pp. 270–273.

Riegler et al. (1999) "Prevalence of HNPCC in a Series of Consecutive Patients on the First Endoscopic Diagnosis of Colorectal Cancer: A Multicenter Study" *Endoscopy* 31:337–341.

Rhyu M. S., (Mar. 6, 1996) "Molecular Mechanisms Underlying Hereditary Nonpolyposis Colorectal Carcinoma," *Journal of the National Cancer Institute*, vol. 88, No. 5, pp. 240–251.

Ridanpaa et al., (1995) "Detection of Loss of Heterozygosity in the p53 Tumor Suppressor Gene Using a PCR–based Assay," *Path. Res. Pract.*, vol. 191, pp. 399–402.

Rodriguez–Bigas et al. (1997) "A National Cancer Institute Workshop on Hereditary Nonpolyposis Colorectal Cancer Syndrome: Meeting Highlights and Bethesda Guidelines" *Journal of the National Cancer Institute* 89:1758–1762.

Salahshor et al. (1999) "Microsatellite Instability in Sporadic Colorectal Cancer is Not an Independent Prognostic Factor" *British Journal of Cancer* 81:190–193.

Samowitz et al. (1995) "Microsatellite Instability in Human Colonic Cancer Is Not a Useful Clinical Indicator of Familial Colorectal Cancer" Gastroenterology 109:1765–1771.

Samowitz et al. (1997) "Microsatellite Instability in Colorectal Adenomas" *Gastroenterology* 112:1515–1519.

Samowitz et al. (1999) "BAT–26 and BAT–40 Instability in Colorectal Adenomas and Carcinomas and Germline Polymorphisms" *American Journal of Pathology* 154:1637–1641.

Sanger et al., (Dec. 1977) "DNA Sequencing with Chain-Terminating Inhibitors" *Proc. Natl. Acad. Sci. USA*, vol. 74, No. 12, pp. 5463–5467.

Santagati et al., (1997) "Quantitation of Low Abundance mRNAs in Glial Cells Using Different Polymerase chain Reaction (PCR)–Based Methods," *Elsevier Science—Brain Research Protocols*, pp. 217–223.

Segel I., (1976), "Double Label Analysis," *Biochemical Calculations*, 2d ed., pp. 373–376.

Sidransky, et al., (Apr. 3, 1992) "Identification of ras Oncogene Mutations in the Stool of Patients with Curable Colorectal Tumors," *Science*, vol. 256, pp. 102–105.

Smith–Ravin et al., (1995) "Detection of c–Ki–ras Mutations in Faecal Samples from Sporadic Colorectal Cancer Patients," *Gut*, vol. 36, pp. 81–86.

Syngal et al. (1998) "Benefits of Colonoscopic Surveillance and Prophylactic Colectomy in Patients With Hereditary Nonpolyposis Colorectal Cancer Mutations" *Annals of Internal Medicine* 129:787–796.

Syngal et al. (1999) "Interpretation of Genetic Test Results for Hereditary Nonpolyposis Colorectal Cancer" *JAMA* 282:247.

Takeda et al., (1993) "Detection of K–ras Mutation in Sputum by Mutant–Allele–Specific Amplification (MASA)," *Human Mutation*, vol. 2, pp. 112–117.

Thibodeau et al., (May 7, 1993) "Microsatellite Instability in Cancer of the Proximal Colon," *Science*, vol. 260, pp. 816–819.

Vasen et al. (1993) "Surveillance in Hereditary Nonpolyposis Colorectal Cancer: An International Cooperative Study of 165 Families" *Diseases of the Colon & Retum* ) 36:1–4.

Vasen et al. (1998) "A Cost–Effectiveness Analysis of Colorectal Screening of Hereditary Nonpolyposis Colorectal Carcinoma Gene Carriers" *American Cancer Society* 82:1632–1637.

Vasen et al. (1999) "New Clinical Criteria for Hereditary Nonpolyposis Colorectal Cancer (HNPCC, Lynch Syndrome) Proposed by the International Collaborative Group on HNPCC" *Gastroentcrology* 116:1453–1456.

Villa et al., (May 1996) "Identification of Subjects at Risk for Colorectal Carcinoma Through a Test Based on K–ras Determination in the Stool," *Gastroenterology*, vol. 110, No. 5, pp. 1346–1353.

Vogelstein, B. and Kinzler, K.W., (Aug., 1999) "Digital PCR," *Proc. Natl. Acad. Sci. USA*, vol. 96, pp. 9236–9241.

Wallace et al., (1979) "Hybridization of Synthetic Oligodeoxyribonucleotides to $\Phi_\chi$ 174 DNA: the Effect of Single Base Pair Mismatch," *Nucleic Acids Research*, vol. 6, No. 11, pp. 3543–3557.

Walsh et al., (Feb. 6, 1992) "Preferential PCR Amplification of Alleles: Mechanisms and Solutions," *PCR Methods and Applications*, pp. 241–250.

Wang et al., (May 15, 1998) "Large–Scale Identification, Mapping, and Genotyping of Single–Nucleotide Olymorphisms in the Human Genome," *Science*, vol. 280, pp. 1077–1082.

Watson et al., "Isolation of Differentiality Expressed Sequence Tags from Human Breast Cancer," *Advances in Brief XP 000576043*, pp. 4598–4602.

Wijnen et al. (1999) "Familial Endometrial Cancer in Female Carriers of MSH6 Germline Mutations" *Nature Genetics* 23:142–144.

Young G.P., and B.H. Demediu, (1992) "The Genetics, Epidemiology, and Early Detection of Gastrointestinal Cancers" *Current Opinion in Oncology*, vol. 4, pp. 728–735.

Zhou et al. (1997) "Allelic Profiles of Mononucleotide Repeat Microsatellites in Control Individuals and in Colorectal Tumors With and Without Replication Errors" *Oncogene* 15:1713–1718.

Zhou et al. (1998) "Determination of the Replication Error Phenotype in Human Tumors Without the Requirement for Matching Normal DNA by Analysis of Mononucleotide Repeat Microsatellites" *Genes, Chromosomes & Cancer* 21:101–107.

Allen et al. (1997), "Morphological and biochemical characterization and analysis of apoptosis." *J. Pharm. & Toxicol. Methods*, vol. 37, No. 4, pp. 215–228.

Ambrosini et al. "A novel anti–apoptosis gene, survivin, expressed in cancer and lymphoma" *Nature Medicine*, vol. 3, No. 8, pp. 917–921, Aug. 1997.

Anker et al., (1999), "Detection of Circulating Tumour DNA in the Blood (plasma/serum) of Cancer Patients," *Cancer and Metastasis Reviews*, vol. 18, pp. 65–73.

Arber et al. "A K–ras Oncogene Increases Resistance to Sulindac–Induced Apoptosis in Rat Enterocytes," *Gastroenterology*, vol. 113, No. 6, pp. 1892–1900, Dec. 1997.

Azhikina et al. (1996), "Factors Affecting the Priming Efficiency of Short Contiguous Oligonucleotide Strings in the Primer Walking Strategy of DNA Sequencing," *DNA Sequence* 6:211–16.

Barry et al. "Identification of Deoxyribonuclease II as an Endonucleas Involved in Apoptosis," *Archives of Biochemistry and Biophysics*, vol. 300, No. 1, pp. 440–448, Jan. 1993.

Bernstein et al. "A Bile–Acid–induced Apoptosis Assay for Colon–Cancer Risk and Associated Quality Control Studies," *Cancer Research*, vol. 59, pp. 2353–2357, May 15, 1999.

Boom et al., (Mar. 1990) "Rapid and Simple Method for Purification of Nucleic Acids" *J. Clin. Microbiol.*, vol. 28, No. 3, pp. 495–503.

Croitoru et al. "Reduce, Reuse, and Recycle: Shedding Light on Shedding Cells," *Gastroenterology*, vol. 105, pp. 1243–1246, Oct. 1993.

Cawkwell et al. (1994), "Frequency of allele loss of DCC, p53, RB1, WT1, NF1, NM23 and APC/MCC in colorectal cancer assayed by fluorescent multiplex polymerase chain reaction." *Brit. J. Can.*, vol. 70, No. 5, pp. 813–818.

Chen et al., (Jul. 15, 1996), "Detection of Single–Base Mutations by a Competitive Mobility Shift Assay," *Analytical Biochemistry, US, Academic, Press*, vol. 239, No. 1, pp. 61–69.

Coombs et al., (May 21, 1996) "A Rapid, Simple, and User–Friendly Method for DNA Extraction from Clinical Stool Samples," *ASM 1996 General Meeting*, New Orleans, LA.

Dennin, (1979), "DNA of Free and Complexed Origin in Human Plasma: Concentration and Length Distribution," *Klin. Wochenschr*, vol. 57, pp. 451–456.

Depractere, "'Eat me' Signals of apoptotic bodies," *Nature Cell Biology*, vol. 2, p. E104, Jun. 2000.

Ditkoff et al. (1996), "Detection of circulating thyroid cells in peripheral blood," *Surgery* vol. 120, No. 6, pp. 959–965.

Eads et al., (1999) "CpG Island Hypermethylation in Human Colorectal Tumors Is Not Associated with DNA Methyltransferase Overexpression." *Cancer Research*, vol. 59, No. 10, pp. 2302–2306.

Echeverria et al., (Sep. 1985) "DNA Hybridization in the Diagnosis of Bacterial Diarrhea," *Clinics in Laboratory Medicine*, vol. 5, No. 3, Sep. 1985, pp. 447–462.

Emlen et al., (1984), "Effect of DNA Size and Strandedness on the in vivo Clearance and Organ Localization of DNA," *Clin. exp. Immunol.*, vol. 56, pp. 185–192.

Finkel "Does Cancer Therapy Trigger Cell Suicide?," *Science*, vol. 286, pp. 2256–2258, Dec. 17, 1999.

Fournie et al., (1995), "Plasma DNA as a Marker of Cancerous Cell Death. Investigations in Patients Suffering from Lung Cancer and in Nude Mice Bearing Human Tumours," *Cancer Letters*, vol. 91, pp. 221–227.

Garewal et al. "Reduced Bile Acide–induced Apoptosis in 'Normal' Colorectal Mucosa: A Potential Biological Marker for Cancer Risk," *Cancer Research*, vol. 56, pp. 1480–1483, Apr. 1, 1996.

Giacona, et al. (1998), "Cell–free DNA in Human Blood plasma: Length Measurements in Patients with Pancreatic Cancer and Healthy Controls," *Pancreas*, vol. 17, No. 1, pp. 89–97.

Halim, "Apoptosis: Orderly Dismantling," *The Scientist*, p. 19, Feb. 7, 2000.

Hall et al. "Regulation of cell number in the mammalian gastrointestinal tract: the importance of apoptosis," *Journal of Cell Science*, vol. 107, pp. 3569–3577, 1994.

Hetts, "To Die or Not to Die, An Overview of Apoptosis and Its Role in Disease," *JAMA*, vol. 279, No. 4, pp. 300–307, Jan. 28, 1998.

Hibi et al., (Apr. 1998), "Molecular Detection of Genetic Alterations in the Serum of Colorectal Cancer Patients," *Cancer Research*, vol. 58, pp. 1405–1407.

Hitchcock, "Actin–Deoxyribonuclease I Interaction," *The Journal of Biochemical Chemistry*, vol. 255, No. 12, pp. 5668–5673, 1980.

Hunsaker, et al. (1989), "Use of Reversible Target Capture to Detect Subattomole Quantities of Target Nonradioleotopically in Crude Specimens in One Hour," *Abstracts of the 89th Meeting of the American Society for Microbiology*, D–169, p. 110.

Ito et al., (1999), "Profile of Circulating Levels of Interleukin–1 Receptor Antagonist and Interleukin–6 in Colorectal Cancer Patients," *Scand. J. Gastroenterol.*, vol. 11, pp. 1139–1143.

Iwanaga et al. "A Novel Mechanism for Disposing of Effete Epithelial Cells in the Small Intestine of Guinea Pigs," *Gastroenterology*, vol. 105, No. 4, pp. 1089–1097, 1993.

Kataoka et al. "Association of high molecular weight DNA fragmentation with apoptotic or non–apoptotic cell death induced by calcium ionophore" *FEBS Letters*, vol. 364, pp. 264–267, 1995.

Kawasaki et al. "Inhibition of Apoptosis by Survivin Predicts Shorter Survival Rates in Colorectal Cancer," *Cancer Research*, vol. 58, pp. 5071–5074, Nov. 15, 1998.

Kishi et al. "Human Serum Deoxyribonuclease I (DNase I) Polymorphism: Pattern Similarities among Isozymes from Serum, Urine, Kidney, Liver, and Pancreas," *Am. J. Hum. Genet.*, vol. 47, pp. 121–126, 1990.

Komano et al. "Homeostatic regulation of intestinal epithelia by intraepithelial γδ T cells" *Proc. Natl. Acad. Sci. USA 92*, vol. 92, pp. 6147–6151, Jun. 1995.

Lefrere et al., (Oct. 1998) "Screening Blood Donations for Viral Genomes: Multicenter Study of Real–Time Simulation Using Pooled Samples on the Model of HCV RNA Detection," *Transfusion*, vol. 38, pp. 915–923.

Leon et al., (Mar. 1977), "Free DNA in the Serum of Cancer Patients and the Effect of Therapy," *Cancer Research*, vol. 37, pp. 646–650.

Li et al., (Aug. 1996) "Rapid Detection of Mycobacterium Avium in Stool Samples from AIDS Patients by Immunomagnetic PCR," *J. Clin. Microbiol.*, vol. 34, No. 8, pp. 1903–1907.

Lipkin, "Biomarkers of Increased Susceptibility to Gastrointestinal Cancer: New Application to Studies of Cancer Prevention in Human Subjects," *Cancer Research*, vol. 48, pp. 235–245, Jan. 15, 1998.

Maebo, (1990), "Plasma DNA Level as a Tumor Marker in Primary Lung Cancer," Japanese; English abstract attached.

Mannherz et al. "A Specific 1:1 G–Actin; DNAase I Complex Formed by the Action of DNAase I on F–Actin," *FEBS Letters*, vol. 60, No. 1, pp. 34–38, Dec. 1975.

Mannherz et al. "The Interaction of Bovine Pancreatic Deoxyribonuclease I and Skeletal Muscle Actin," *Eur. J. Biochem*, vol. 104, pp. 367–379, 1980.

Metspalu A., "Arrayed Primer Extension (APEX) for Mutation Detection Using Gene–Specific DNA Chips" *European Society of Human Genetics*, vol. 6, No. Sup 1, 1998, p. PL36 XP000892253 Abstract.

Morandi et al., (Jun. 1998) "Detection of HIV Type 1 RNA in Pools of Sera Negative for Antibodies to HIV–1 and HIV–2," *J. of Clinical Microbiology*, vol. 36, No. 6, pp. 1534–1538.

Morrissey et al., (May 14–18, 1989) "Novel Hybridization Technique with Subattomole Sensitivity in Specimens," *American Society for Microbiology*, 89th Annual Meeting, Abstract D–168, p. 110.

Morrissey, et al., (Sep. 1989) "Nucleic Acid Hybridization Assays Employing dA–Tailed Capture Probes," *Analytical Biochemistry*, vol. 181, No. 2, pp. 345–359.

Morrissey, D. and Collins, M., (Jun. 1989) "Nucleic Acid Hybridization Assays Employing dA–Tailed Capture Probes: Single Capture Methods," *Mol. And Cell. Probes*, vol. 3, No. 2, pp. 189–207.

Mulcahy et al. (1998), "A prospective study of K–ras mutations in the plasma of pancreatic cancer patients," *Clin. Cancer Res.*, vol. 4, pp. 271–275.

Olive, (Feb. 1989) "Detection of Enterotoxigenic *Escherichia coli* after Polymerase Chain Reaction Amplification with a Thermostable DNA Polymerase," *Journal of Clinical Microbiology*, vol. 27, No. 2, pp. 261–265.

Paabo et al., (1988) "Mitochondrial DNA Sequences from 7000–year old Brain," *Nucleic Acids Research*, vol. 16, No. 20, pp. 9775–9787.

Pacek et al., (May 1993) "Determination of Allele Frequencies at Loci with Length Polymorphism by Quantitative Analysis of DNA Amplified from Pooled Samples," *PCR Methods and Applications*, vol. 2, No. 4, pp. 313–317.

Park et al. "Detergent and Enzyme Treatment of Apoptotic Cells for Observation of DNA Fragmentation," *BioTechniques*, vol. 24, No. 4, pp. 558–559, 1998.

Payne et al. "Role of Apoptosis in Biology and Pathology: Resistance to Apoptosis in Colon Carcinogenesis," *Ultrastructural Pathology*, vol. 19, pp. 221–248, 1995.

Peitsch et al. "Characterization of the endogenous deoxyribonuclease involved in nuclear DNA degration during apoptosis (programmed cell death)," *The EMBO Journal*, vol. 12, No. 1, pp. 371–377, 1993.

Peitsch et al. "Functional characterisation of serum DNase I in MRI," *Biochemical and Biophysical Research Communications*, vol. 186, No. 2, pp. 739–745, Jul. 31, 1992.

Peitsch et al. "The apoptosis endonucleases: cleaning up after cell death?," *Trends in Cell Biology*, vol. 4, pp. 37–41, Feb. 4, 1994.

Polzar et al. "Distribution of deoxyribonuclease 1 in rat tissues and its correlation to cellular turnover and apoptosis (programmed cell death)," *European Journal of Cell Biology*, vol. 64, pp. 200–210, 1994.

Polzar et al. "Overexpression of deoxyribonuclease I (DNase I) transfected into COS–cells: its distribution during apoptotic cell death," *European Journal of Cell Biology*, vol. 62, pp. 397–405, 1993.

Raptis et al., (Dec. 1980), "Quantitation and Characterization of Plasma DNA in Normals and Patients with Systemic Lupus Erythematosus," *J. Clin. Invest.*, vol. 66, pp. 1391–1399.

Rinaldy et al. (1988), "Gene Cloning Using cDNA Libraries in a Differential Competition Hybridization Strategy: Application to Cloning XP–A Related Genes," *DNA* vol. 7, No. 8, pp. 563–570.

Ruzicka et al., (1992) "Apolipoprotein Allele Specific PCR: Large–Scale Screening of Pooled Blood Samples," *J. of Lipid Research*, vol. 33, pp. 1563–1567.

Saitoh et al. "Analysis of Bcl–2, Bax and Survivin genes in uterine cancer," *International Journal of Oncology*, vol. 15, pp. 137–141, 1999.

Sales et al., (Jul. 31, 1999), "Blood Dissemination of Colonic Epithelial Cells During No–touch Surgery for Rectosigmoid Cancer," *The Lancet*, vol. 354, p. 392.

Samiotaki et al. (1994), "Dual–Color Detection of DNA Sequence Variants by Ligase–Mediated Analysis," *Genomics* 20:238–42.

Schmitt et al. (1998), "Bax–alpha promotes apoptosis induced by cancer chemotherapy and accelerates the activation of caspase 3–like cysteine proteases in p53 double mutant B lymphoma Namalwa cells," *Cell Death & Diff.*, vol. 5, No. 6, pp. 506–16.

Sen "Programmed Cell Death: Concept, Mechanism and Control," *Biol. Rev.*, vol. 67, pp. 287–319, 1992.

Shapiro et al., (Jun. 1, 1983), "Determination of Circulating DNA Levels in Patients with Benign or Malignant Gastrointestinal Disease," *Cancer*, vol. 51, No. 11, pp. 2116–2120.

Shaw et al., (1998) "Allele Frequency Distribution in Pooled DNA Samples, Applications to Mapping Complex Disease Genes," *Genome Research*, vol. 8, pp. 111–123.

Sidransky, D. (1997) "Nucleic acid–based methods for the detection of cancer," *Science*, vol. 278, No. 5340, pp. 1054–1058.

Skoletsky et al. (1998) "High frequency of detecting amplifiable DNA in stools of apparently normal individuals," *Gastroenterology*, vol. 114, No. 4, p. A681.

Sträter et al. "Rapid Onset of Apoptosis In Vitro Follows Disruption of B1 Integrin/Matrix Interactions in Human Colonic Crypt Cell" *Gastroenterology*, vol. 110, No. 6, pp. 1776–1784, Jun. 1996.

Stroun et al., (1987), "Isolation and Characterization of DNA from the Plasma of Cancer Patients," *Eur. J. Cancer Clin. Oncol.*, vol. 23, No. 6, pp. 707–712.

Tompkins et al., (1986) "Approaches to the Detection of Enteric Pathogens, Including *Campylobacter*, using Nucleic Acid Hybridization," *Diagn. Microbiol, Infect. Dis.*, vol. 4, pp. 71S–78S.

Tsujitani et al. "Apoptotic Cell Death and Its Relationship to Carcinogenesis in Colorectal Carcinoma," *Cancer Supplement*, vol. 77, No. 8, pp. 1711–1716, Apr. 15, 1996.

Vera–Garcia, et al., (May 16–20, 1993) "Development and Evaluation of an Instrument Designed to Reproducibly Release Nucleic Acids from Microorganisms," *American Society for Microbiology: Polymerase Chain Reaction*, 93rd General Meeting, Session 214, Abstract C–217, p. 484.

Vet et al., (1998) "Comparative analysis of p53 mutations in bladder washings and histologic specimens," *Am. J. Clin. Path.*, vol. 110, No. 5, pp. 647–652.

Vogelstein et al., (1979) "Preparative and Analytical Purification of DNA from Agarose," *Proc. Natl. Acad. Sci. USA*, vol. 76, No. 2, pp. 615–619.

Wagner et al. "Regulation of Gastric Epithelial Cell Growth by Helicobacter pylori: Evidence for a Major Role of Apoptosis," *Gastroenterology*, vol. 113, No. 6, pp. 1836–1847, Dec. 1997.

Walsh et al., (1991) "Chelex® 100 as a Medium for Simple Extraction of DNA for PCR–Based Typing from Forensic Material," *BioTechniques*, vol. 10, No. 4, pp. 506–513.

Walton et al., (1997) "A PCR–Based Method for Detecting Rare Genotypes in Large Samples of Individuals," *Mol. Ecology*, vol. 6, No. 2, pp. 195–197.

Zhang et al. "Quantitative determination of apoptotic death in cultured human pancreatic cancer cells by propidium iodide and digitonin," *Cancer Letters*, vol. 142, pp. 129–137, 1999.

Ahlquist et al., "Colorectal Cancer Screening by Detection of Altered Human DNA in Stool: Feasibility Multitarget Assay Panel," Presented at Digestive Disease Week Annual Conference, Orlando, FL, May 19, 1999 (*Gastroenterology*, 119, pp. 1219–1227(2000)).

Ahlquist et al., "Universal Detection of Aerodigestive Cancers by Assay of Nonapoptotic Human DNA in Stool," Presented at Digestive Disease Week Annual Conference, San Diego, CA, May 2000.

Makristathis et al., "Detection of Helicobacter pylori in Stool Specimen by PCR and Antigen Enzyme Immunoassay," *Journal of Clinical Microbiology*, vol. 36, No. 9, pp. 2772–2774, Sep. 1998.

Böhm et al. (1997), "Deletion Analysis at the DEL–27, APC and MTSI Loci in Bladder Cancer: LOH at the DEL–27 Locus on 5p13–12 is a Prognostic Marker of Tumor Progression," *Int. J. Cancer (Pred. Oncol.)*, 74:291–295.

Hickman et al. (1994), "Apoptosis and cancer chemotheraphy," *Phil. Trans R. Soc. Lond.*, 345:319–325.

Kawakami et al. (2000), "Hypermethylated APC DNA in Plasma and Prognosis of Patients with Esophageal Adenocarcinoma," *Journal of the National Cancer Institute*, 92(22):1805–1811.

Ko et al. (1999), "Genomic Instability and Alterations in Apc, Mcc and Dcc in Hong Kong Patients with Colorectal Carcinoma," *Int. J. Cancer (Pred. Oncol.)*, 84:404–409.

\* cited by examiner

200bp
AMPLIFICATIONS
33 CYCLES

| LANE | Q# | SAMPLE TYPE | SAMPLE NUMBER | GRADE |
|---|---|---|---|---|
| 1 | 7903.8 | ABNORMAL | 1 | A |
| 2 | 5627.4 | ABNORMAL | 2 | A |
| 3 | 8809.11 | ABNORMAL | 3 | A |
| 4 | 5421.94 | ABNORMAL | 4 | A |
| 5 | 1838.07 | POSITIVE CONTROL | | B |
| 6 | -549.23 | NORMAL | 5 | C |
| 7 | -715 | NORMAL | 6 | C |
| 8 | -1605.13 | NORMAL | 7 | C |
| 9 | -824.73 | NORMAL | 8 | C |
| 10 | 259.77 | NORMAL | 9 | C |
| 11 | | NEG CONTROL | - | |
| 12 | | NEG CONTROL | - | |
| 13 | 400 | 400 | STANDARD | |
| 14 | 2000 | 2000 | STANDARD | |
| 15 | 4000 | 4000 | STANDARD | |
| 16 | 6000 | 6000 | STANDARD | |
| 17 | 8000 | 8000 | STANDARD | |
| 18 | 10000 | 10000 | STANDARD | |

A= >2000
B= 500-2000
C= <500

200bp
AMPLIFICATIONS
35 CYCLES

| LANE | Q# | SAMPLE TYPE | SAMPLE NUMBER | GRADE |
|---|---|---|---|---|
| 1 | 10851.04 | ABNORMAL | 1 | A |
| 2 | 8862.34 | ABNORMAL | 2 | A |
| 3 | 9777.85 | ABNORMAL | 3 | A |
| 4 | 6874.28 | ABNORMAL | 4 | A |
| 5 | 2392.07 | POSITIVE CONTROL | | B |
| 6 | 3080.62 | NORMAL | 5 | B |
| 7 | 813.45 | NORMAL | 6 | C |
| 8 | -720.04 | NORMAL | 7 | C |
| 9 | -442.2 | NORMAL | 8 | C |
| 10 | 1353.86 | NORMAL | 9 | B |
| 11 | | NEG CONTROL | - | |
| 12 | | NEG CONTROL | - | |
| 13 | 400 | 400 | STANDARD | |
| 14 | 2000 | 2000 | STANDARD | |
| 15 | 4000 | 4000 | STANDARD | |
| 16 | 6000 | 6000 | STANDARD | |
| 17 | 8000 | 8000 | STANDARD | |
| 18 | 10000 | 10000 | STANDARD | |

A= >5000
B= 1000-5000
C= <1000

200bp
AMPLIFICATIONS
34 CYCLES

| LANE | Q# | SAMPLE TYPE | SAMPLE NUMBER | GRADE |
|---|---|---|---|---|
| 1 | 8428.34 | ABNORMAL | 1 | A |
| 2 | 4917.31 | ABNORMAL | 2 | A |
| 3 | 7742.22 | ABNORMAL | 3 | A |
| 4 | 3049.85 | ABNORMAL | 4 | A |
| 5 | 409.5 | POSITIVE CONTROL | | B |
| 6 | -682.75 | NORMAL | 5 | C |
| 7 | -781.09 | NORMAL | 6 | C |
| 8 | -1099.28 | NORMAL | 7 | C |
| 9 | -1015.39 | NORMAL | 8 | C |
| 10 | 359.74 | NORMAL | 9 | B |
| 11 | | NEG CONTROL | - | |
| 12 | | NEG CONTROL | - | |
| 13 | 400 | 400 | STANDARD | |
| 14 | 2000 | 2000 | STANDARD | |
| 15 | 4000 | 4000 | STANDARD | |
| 16 | 6000 | 6000 | STANDARD | |
| 17 | 8000 | 8000 | STANDARD | |
| 18 | 10000 | 10000 | STANDARD | |

A= >750
B= 250-750
C= <250

200bp
AMPLIFICATIONS
33 CYCLES

| LANE | Q# | SAMPLE TYPE | SAMPLE NUMBER | GRADE |
|---|---|---|---|---|
| 1 | 7879.15 | ABNORMAL | 1 | A |
| 2 | 4079.09 | ABNORMAL | 2 | A |
| 3 | 7995.95 | ABNORMAL | 3 | A |
| 4 | 2600.3 | ABNORMAL | 4 | A |
| 5 | 1698.19 | POSITIVE CONTROL | | B |
| 6 | -405.32 | NORMAL | 5 | C |
| 7 | -466.15 | NORMAL | 6 | C |
| 8 | -1046.47 | NORMAL | 7 | C |
| 9 | -764.83 | NORMAL | 8 | C |
| 10 | 105.05 | NORMAL | 9 | C |
| 11 | | NEG CONTROL | - | |
| 12 | | NEG CONTROL | - | |
| 13 | 400 | 400 | STANDARD | |
| 14 | 2000 | 2000 | STANDARD | |
| 15 | 4000 | 4000 | STANDARD | |
| 16 | 6000 | 6000 | STANDARD | |
| 17 | 8000 | 8000 | STANDARD | |
| 18 | 10000 | 10000 | STANDARD | |

A= >2000
B= 500-2000
C= <500

200bp
AMPLIFICATIONS
34 CYCLES

| LANE | Q# | SAMPLE TYPE | SAMPLE NUMBER | GRADE |
|---|---|---|---|---|
| 1 | 7852.95 | ABNORMAL | 1 | A |
| 2 | 4797.07 | ABNORMAL | 2 | A |
| 3 | 8543.47 | ABNORMAL | 3 | A |
| 4 | 3597.23 | ABNORMAL | 4 | A |
| 5 | 943.84 | POSITIVE CONTROL | | B |
| 6 | -296.7 | NORMAL | 5 | C |
| 7 | -5.48 | NORMAL | 6 | C |
| 8 | -896.94 | NORMAL | 7 | C |
| 9 | -196.87 | NORMAL | 8 | C |
| 10 | 414.81 | NORMAL | 9 | C |
| 11 | | NEG CONTROL | - | |
| 12 | | NEG CONTROL | - | |
| 13 | 400 | 400 | STANDARD | |
| 14 | 2000 | 2000 | STANDARD | |
| 15 | 4000 | 4000 | STANDARD | |
| 16 | 6000 | 6000 | STANDARD | |
| 17 | 8000 | 8000 | STANDARD | |
| 18 | 10000 | 10000 | STANDARD | |

A= >2000
B= 500-2000
C= <500

200bp
AMPLIFICATIONS
34 CYCLES

| LANE | Q# | SAMPLE TYPE | SAMPLE NUMBER | GRADE |
|---|---|---|---|---|
| 1 | 7660.6 | ABNORMAL | 1 | A |
| 2 | 7032.89 | ABNORMAL | 2 | A |
| 3 | 8364.31 | ABNORMAL | 3 | A |
| 4 | 6892.04 | ABNORMAL | 4 | A |
| 5 | 4883.47 | POSITIVE CONTROL | | A |
| 6 | 1934.67 | NORMAL | 5 | B |
| 7 | 1380.64 | NORMAL | 6 | B |
| 8 | -964.17 | NORMAL | 7 | C |
| 9 | 1729.51 | NORMAL | 8 | B |
| 10 | 2221.69 | NORMAL | 9 | B |
| 11 | | NEG CONTROL | - | |
| 12 | | NEG CONTROL | - | |
| 13 | 400 | 400 | STANDARD | |
| 14 | 2000 | 2000 | STANDARD | |
| 15 | 4000 | 4000 | STANDARD | |
| 16 | 6000 | 6000 | STANDARD | |
| 17 | 8000 | 8000 | STANDARD | |
| 18 | 10000 | 10000 | STANDARD | |

A= >5000
B= 1000-5000
C= <1000

200bp
AMPLIFICATIONS
33 CYCLES

| LANE | Q# | SAMPLE TYPE | SAMPLE NUMBER | GRADE |
|---|---|---|---|---|
| 1 | 8519.13 | ABNORMAL | 1 | A |
| 2 | 5745.19 | ABNORMAL | 2 | A |
| 3 | 9765.65 | ABNORMAL | 3 | A |
| 4 | 4153.79 | ABNORMAL | 4 | A |
| 5 | 1869.33 | POSITIVE CONTROL | | B |
| 6 | 418.37 | NORMAL | 5 | C |
| 7 | 405.91 | NORMAL | 6 | C |
| 8 | -258.08 | NORMAL | 7 | C |
| 9 | 141.64 | NORMAL | 8 | C |
| 10 | 450.78 | NORMAL | 9 | C |
| 11 | | NEG CONTROL | - | |
| 12 | | NEG CONTROL | - | |
| 13 | 400 | 400 | STANDARD | |
| 14 | 2000 | 2000 | STANDARD | |
| 15 | 4000 | 4000 | STANDARD | |
| 16 | 6000 | 6000 | STANDARD | |
| 17 | 8000 | 8000 | STANDARD | |
| 18 | 10000 | 10000 | STANDARD | |

A= >2000
B= 500-2000
C= <500

1.8kb
AMPLIFICATIONS
36 CYCLES

| LANE | Q# | SAMPLE |
|---|---|---|
| 1 | | NEG CONTROL |
| 2 | 102.935 | ABNORMAL |
| 3 | 260.645 | ABNORMAL |
| 4 | 0.075 | NORMAL |
| 5 | 48.305 | ABNORMAL |
| 6 | 0.045 | NORMAL |
| 7 | 18.575 | NORMAL |
| 8 | | NEG CONTROL |
| 9 | | NEG CONTROL |
| 10 | 75 | 75 |
| 11 | 125 | 125 |
| 12 | 250 | 250 |
| 13 | 500 | 500 |
| 14 | 1000 | 1000 |

ABNORMAL / NORMAL CUTOFF  40

| 1.8kb AMPLIFICATIONS 38 CYCLES LANE | Q# | SAMPLE |
|---|---|---|
| 1 |  | NEG CONTROL |
| 2 | 81.84 | ABNORMAL |
| 3 | 91.515 | ABNORMAL |
| 4 | 0.04 | NORMAL |
| 5 | 24.86 | ABNORMAL |
| 6 | 0.88 | NORMAL |
| 7 | 17.25 | NORMAL |
| 8 |  | NEG CONTROL |
| 9 |  | NEG CONTROL |
| 10 | 75 | 75 |
| 11 | 125 | 125 |
| 12 | 250 | 250 |
| 13 | 500 | 500 |
| 14 | 1000 | 1000 |

ABNORMAL / NORMAL CUTOFF  20

SEQUENCE LISTING

```
<160> NUMBER OF SEQ ID NOS: 7

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: K-ras
      oligonucleotide probe

<400> SEQUENCE: 1
gtggagtatt tgatagtgta ttaaccttat gtgtgac                              37

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence:apc-1309
      oligonucleotide probe

<400> SEQUENCE: 2
ttccagcagt gtcacagcac cctagaacca aatccag                              37

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence:apc-1378
      oligonucleotide probe

<400> SEQUENCE: 3
cagatagccc tggacaaaca atgccacgaa gcagaag                              37

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence:first p53
      oligonucleotide probe

<400> SEQUENCE: 4
tactcccctg ccctcaacaa gatgttttgc caactgg                              37

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: second p53
      oligonucleotide probe

<400> SEQUENCE: 5
```

```
                                            -continued
atttcttcca tactactacc catcgacctc tcatc                                      35

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence:third p53
      oligonucleotide probe

<400> SEQUENCE: 6
atgaggccag tgcgccttgg ggagacctgt ggcaagc                                    37

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence:fourth p53
      oligonucleotide probe

<400> SEQUENCE: 7
gaaaggacaa gggtggttgg gagtagatgg agcctgg                                    37
```

METHODS FOR DETECTING NUCLEIC ACIDS INDICATIVE OF CANCER

This application claims benefit of U.S. provisional patent application, Ser. No. 60/128,629 field Apr. 9, 1999, the disclosure of which is incorporated by reference herein.

FIELD OF THE INVENTION

This invention relates to methods for the early detection of cancer in patients by screening for large DNA fragments. Methods of the invention are especially useful in the detection of colon cancer.

BACKGROUND OF THE INVENTION

Alterations in genomic integrity often are associated with disease or with the propensity for disease. For example, many cancers are thought to arise through a series of mutations in genomic DNA, resulting in genomic instability in the form of uncontrolled cellular growth. In normal cells, damage to genomic DNA typically leads to expression of tumor suppressors, such as the cell-cycle regulator, p53. For example, damage to cellular DNA results in increased expression of p53 which arrests the cell cycle to allow repair of the damage. If the damaged DNA cannot be repaired, the cell undergoes apoptosis, thus preventing the accumulation of additional mutations in daughter cells. If however, there is a mutation in the p53 gene itself (or in another cell cycle regulator), damaged cells will proceed through the cell cycle, giving rise to progeny in which additional DNA mutations will go unchecked. It is the accumulation of these mutations that is the hallmark of many cancers.

The process of apoptosis is important not only in the regulation of cellular metabolism, but also in inhibiting oncogenesis. As cells undergo apoptosis, the nucleus becomes small and fragmented. Nuclear DNA is digested into spindle fragments that are generally no larger than about 200 base pairs. As the process continues, usually through multiple pathways, the cell membrane breaks down, and cellular contents are metabolized. As a result, cells that have the potential to enter the multi-step pathway leading to cancer are eliminated.

Many cancers are curable if detected early in their development. For example, colorectal cancers typically originate in the colonic epithelium, and are not extensively vascularized (and therefore not invasive) during early stages of development. The transition to a highly-vascularized, invasive and ultimately metastatic cancer commonly takes ten years or longer. If the presence of cancer is detected prior to extensive vascularization, surgical removal typically is an effective cure. However, colorectal cancer is often detected only upon manifestation of clinical symptoms, such as pain and black tarry stool. Generally, such symptoms are present only when the disease is well established, and often after metastasis has occurred. Early detection of colorectal cancer therefore is important in order to significantly reduce its morbidity.

Invasive diagnostic methods, such as endoscopic examination, allow direct visual identification, removal, and biopsy of potentially-cancerous tissue. Endoscopy is expensive, uncomfortable, inherently risky, and not a practical tool for early diagnosis.

Established non-invasive screening methods involve assaying stool samples for the presence of fecal occult blood or for elevated levels of carcinoembryonic antigen, both of which are suggestive of the presence of colorectal cancer. Additionally, recent developments in molecular biology provide methods of great potential for detecting the presence of a range of DNA mutations indicative of colorectal cancer. The presence of such mutations can be detected in DNA found in stool samples during various stages of colorectal cancer. However, stool comprises cells and cellular debris from the patient, from microorganisms, and from food, resulting in a heterogeneous population of cells. This makes detection of small, specific subpopulations difficult to detect reliably.

There is a need in the art for additional non-invasive methods for early diagnosis of cancer that will detect characteristics indicative of the presence of cancer.

SUMMARY OF THE INVENTION

The present invention provides methods for identifying indicia of cancer in tissue or body fluid samples by identifying non-apoptotic DNA in those samples. The invention also provides methods for identifying indicia of cancer or precancer in samples containing exfoliated epithelial cells. It has now been recognized that DNA obtained from exfoliated normal (non-cancerous) cells is different than DNA obtained from exfoliated cancer or precancer cells. Normal exfoliated cells typically have undergone apoptosis, and thus produce cells or cellular debris (depending upon the stage of apoptosis) comprising DNA that has been substantially degraded. Exfoliated cancer or precancer cells typically have not undergone apoptosis, and such cells or their debris, while producing some very small fragments as a result of degradation in the sample, typically also contain a higher proportion of large DNA fragments (compared to those observed in cells or debris from exfoliated normal cells). The difference in DNA integrity between normal and abnormal cells is a marker for the presence of cancer or precancer in a sample comprising exfoliated cells.

Stool is a good sample for exemplification of methods of the invention. The colonic epithelium undergoes a continual process of exfoliation. Normal epithelial cells undergo apoptosis, and are sloughed into the lumen of the colon, and onto forming stool. Cells from polyps and tumors are also sloughed onto forming stool. However, cells from polyps or tumors are, by definition, not apoptotic. Methods of the invention take advantage of the different characteristics between apoptotic and non- apoptotic cells in order to screen patient samples for indicia of cancer or precancer.

As noted above, non-cancerous (normal) cells undergo apoptosis at regular intervals, or in response to irreparable cell damage. As a result of apoptosis, DNA from normal cells is cleaved into small fragments having about 200 or fewer base pairs, and typically 180 base pairs or less. In contrast, DNA obtained from cancer or precancer cells is much larger than the typical apoptotic fragments. Thus, the presence of large DNA fragments in a sample (e.g., of sloughed colonic epithelium) indicates that there are or were cells in the sample (or the specimen from which it was obtained) that have avoided apoptosis, and its coincidental degradation of DNA. The presence of large DNA fragments represents a positive screen for cancer or precancer.

Accordingly, methods of the invention comprise detecting the presence in a biological sample of species-specific nucleic acids indicative of cancer or precaner. Samples comprising such nucleic acids are identified as having indicia of cancer or precancer. In preferred methods, patients presenting samples having a high proportion of non-apoptotic nucleic acids as determined by methods of the Invention are further evaluated for the presence of a tumor, adenoma, or other cancerous or precancerous lesion.

In general, methods of the invention comprise detecting in a biological sample one or more DNA fragment(s) of a length that would not be substantially present in noncancerous cells or cellular debris. In a preferred embodiment, such fragments are larger than a typical apoptotic spindle fragment, or larger than about 170 base pairs. However, also in a preferred embodiment, methods of the invention comprise detecting DNA fragments that are greater than about 200 base pairs, and preferably greater than about 500 base pairs. There is no upper limit on these fragments, as all that is necessary is that the fragment be larger than an apoptotic fragment. Typically, however, fragments indicative of cancer or precancer cells are between about 200 and about 3500 base pairs, and ideally between about 500 and about 2500 base pairs.

Accordingly, in a preferred embodiment, methods of the invention comprise detecting in a tissue or body fluid sample the presence of nucleic acid fragments having greater than about 500 base pairs or having a molecular weight corresponding to greater than about 500 base pairs. In other preferred embodiments, methods of the invention comprise detecting nucleic acid fragments having between about 200 and about 1000 base pairs, preferably between about 200 and about 600 base pairs, and most preferably about 500 base pairs.

Also in a preferred embodiment, methods of the invention comprise determining a ratio of large fragments (200–3500 bp) to small fragments (less than 200 bp), and determining whether the ratio exceeds an empirically-derived threshold. The threshold is determined empirically by analyzing ratios of large-to-small fragments, and correlating those ratios with the disease state of a selected population of normal and cancer patients. In preferred embodiments, amounts of large and small fragments are determined by polymerase chain reaction amplification of sample DNA using primers selected to amplify long and short fragments. Alternatively, amounts of large and small fragments are determined using the same primer.

Preferred methods of the invention comprise amplifying nucleic acids in a representative stool sample using human-specific primers, and detecting amplicons 5 having greater than about 200, and preferably about 500 or more base pairs. In a highly-preferred embodiment, amplification is accomplished by polymerase chain reaction (PCR) using forward and reverse primers directed against human-specific nucleic acid fragments, and spaced apart to provide a lower limit on the resulting amplicons. Also in a highly-preferred embodiment, primers for PCR are directed against human oncogene or tumor suppressor sequences. Preferred target nucleic acids for PCR primers include p53, Kras, apc, dcc, and other genes known or suspected to be associated with cancer, and especially colorectal cancer. Methods for conducting PCR are provided in U.S. Pat. No. 4,683,202, incorporated by reference herein. The presence of amplicon greater than about 200 base pairs in length is indicative of template nucleic acid in the sample of that length (or longer). According to methods of the invention such long sequences represent a positive screen, and are indicative of cancer or precancer.

Preferred biological samples include stool, pus and urine. Method of the inventions are especially useful for the detection of large DNA fragments in samples comprising exfoliate. Tissue (e.g., colon, lungs, bladder) in which cells, especially epithelial cells, are exfoliated are most preferred for screening methods of the invention. In such tissues, continuing cellular renewal requires that cells are regularly sloughed after having undergone apoptosis. Samples of the exfoliate (tissue or body fluid containing the exfoliated cells) predominantly comprise apoptotic DNA.

Preferred methods of the invention for use on a stool sample comprise obtaining a representative stool sample. An especially-preferred method for preparing a stool sample is disclosed in U.S. Pat. No. 5,741,650, and in co-owned, co-pending U.S. patent application Ser. No. 09/059,713, each of which is incorporated by reference herein.

In a preferred embodiment, methods of the invention comprise homogenizing a representative stool sample in a solvent in order to form a homogenized sample mixture having a solvent volume to stool mass ratio of at least 5 to 1. An especially-preferred ratio of solvent volume to stool mass is about 20:1. A preferred solvent for preparing stool samples according to the invention is a physiologically-compatible buffer comprising a detergent and a proteinase and optionally a DNase inhibitor, such as a buffer comprising Tris-EDTA-NaCl. A preferred buffer is 50 mM Tris, 150 mM EDTA and 10 mM NaCl at pH 9.0. Another preferred solvent is guanidine isothiocyanate (GITC). Providing an optimal solvent volume to stool mass ratio increases the yield of nucleic acid generally from the sample. Further details regarding sample preparation are disclosed in co-owned, co-pending U.S. patent application Ser. No. 09/198,083 incorporated herein by reference.

Preferred methods of the invention further comprise enriching sample for human DNA. Preferred enrichment methods for use in the invention include enriching a desired human target sequence using an affinity column, sequence-specific capture, or through the use of preferred buffers that bias isolation of human DNA. A preferred enrichment method is based upon the capture of unique human nucleic acids using, for example, an affinity column. Details of such methods are provided below.

In a preferred embodiment, methods further comprise the step of extracting DNA from the homogenized sample mixture using sequence-specific nucleic acid probes. Particularly preferred are probes hybridizing to human DNA. The probes are preferably labeled. Preferred labels include radioactive labels, fluorescent labels, molecular weight labels and enzymatic labels. Other labels are well known in the art.

In a preferred embodiment gel electrophoresis, affinity chromatography, or mass spectrometry are used to detect large DNA fragments (fragments comprising greater than about 200 base pairs). The presence of large DNA fragments in the sample is indicative of colorectal cancer.

In a preferred embodiment capture probes comprise DNA, RNA or PNA, and are detectably labeled using methods known in the art. In one embodiment probes are labeled with radioactive isotopes such as $^{32}P$, $^{33}P$, $^{35}S$, $^{125}I$, or any other detectable isotope useful for labeling a hybridization probe. In an another embodiment, probes are labeled with fluorescent molecules. Numerous fluorescent labels are known in the art, and any detectable fluorescent probe label is useful for practice of the invention. Alternatively, probes are attached to moieties which increase their molecular weight. For example a probe may be directly attached to a glycoprotein, or a glass bead, or any compound which has a detectable effect on the molecular weight of the probe. In a further embodiment, probes are labeled with a compound that is detectable due to specific interactions with an additional compound. For example, biotinylated probes are detectable via interaction with streptavidin. The streptavidin moiety is attached to a detectable label such as a bead, a fluorescent tag, or an enzyme. In another example, the probes are labeled with a hapten or other antigen which is specifically recognized by an antibody. The antibody is made detectable using methods known in the art including radioactive isotopes, fluorescent tags, and enzyme reactions. In a further example the probes are directly attached to an enzyme which is detectable via a specific enzyme catalyzed reaction generating a detectable product.

Finally, methods of the invention allow one to approximate the position in the colon of a colorectal lesion based upon the relative amount of DNA fragments in a stool sample that are greater than 200 base pairs in length. This aspect of the invention relies on the fact that the lytic properties of stool are greater in the proximal colon than they are in the distal colon. In the proximal colon, stool is typically in liquid form. Therefore, the cell lysis and DNA degrading enzymes in the colon have greater access to exfoliated cells in the liquid mixture of the proximal colon as compared to their access to exfoliated cells sloughed onto formed or forming stool that is typical in the distal colon. As a consequence of the differences between the environments of the proximal and distal colon, the present invention provides that typical DNA fragments from cells exfoliated into the proximal colon are smaller than DNA fragments from cells exfoliated into the distal colon. FIG. 1 provides an example of the progression of DNA sizes expected for cancer or precancer cells exfoliated into different regions of the colon. The size of DNA fragments from noncancerous or precancerous cells is the same throughout the colon due to the fact that the DNA from those cells is degraded primarily through apoptosis. Thus, cell lysis and DNA degradation play only minor roles in determining the size of DNA fragments from most exfoliated normal cells throughout the colon. It is noted, however, that normal cells that are, for example, mechanically sheared from the colon undergo the same lytic and degradation cycle as the typical cancer or precancer cell. However, the contribution of such non-apoptotic normal cells to the overall level of DNA in the stool sample is small, and is controlled for by establishing standards as taught below.

Further aspects and advantages of the invention are contained in the following detailed description thereof.

DETAILED DESCRIPTION OF THE INVENTION

Figure 1:
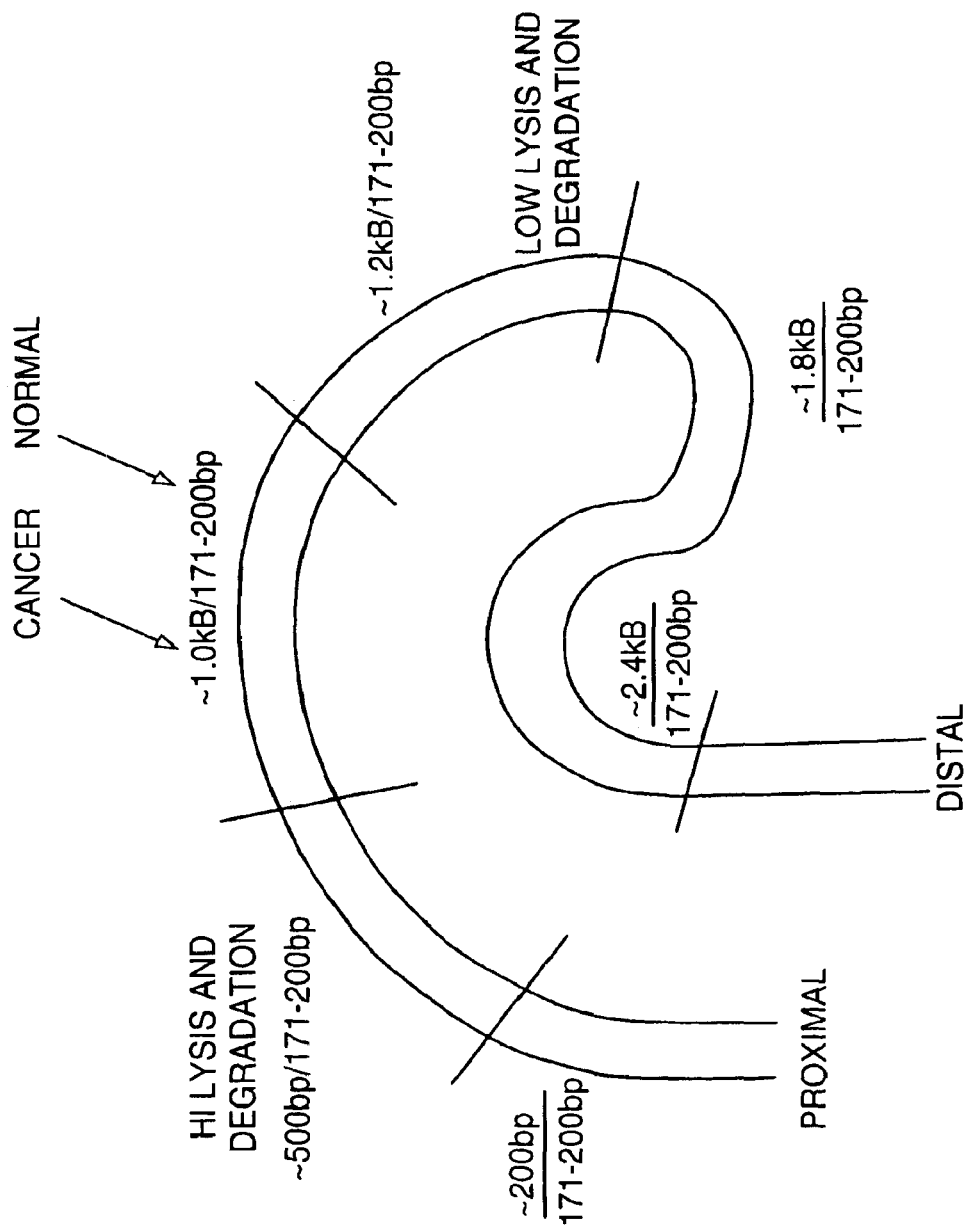
FIG. 1 shows a schematic representation of the colon, and the representative (typical) DNA fragment length for DNA obtained from a cancer or precancer exfoliated cell over the representative (typical) apoptotic (normal) DNA fragment length for various regions of the colon.
Figure 2:
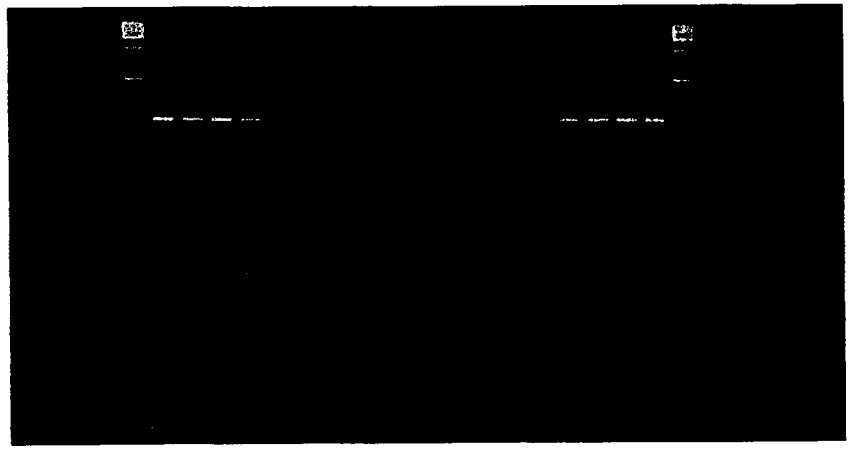
FIG. 2 is a gel photograph showing results of amplification of Kras (exon 1) DNA isolated from stool using forward and reverse primers spaced about 200 bp apart. The band Intensity relates to the amount of 200 bp product or greater in the sample. Lanes 1–4 are results from patients with cancer or adenoma, lane 5 is a positive control, lanes 6–10 are from patients who did not have cancer or adenoma, lanes 11–12 are negative controls, and lanes 13–18 are standards at the approximate molecular weight indicated in the figure.
Figure 3:
FIG. 3 is a gel photograph showing results of amplification of apc (exon 15) DNA isolated from stool using forward and reverse primers spaced about 200 bp apart. The band intensity relates to the amount of 200 bp product or greater in the sample. Lanes 1–4 are results from patients with cancer or adenoma, lane 5 is a positive control, lanes 6–10 are from patients who did not have cancer or adenoma, lanes 11–12 are negative controls, and lanes 13–18 are standards at the approximate molecular weight indicated in the figure.
Figure 4:
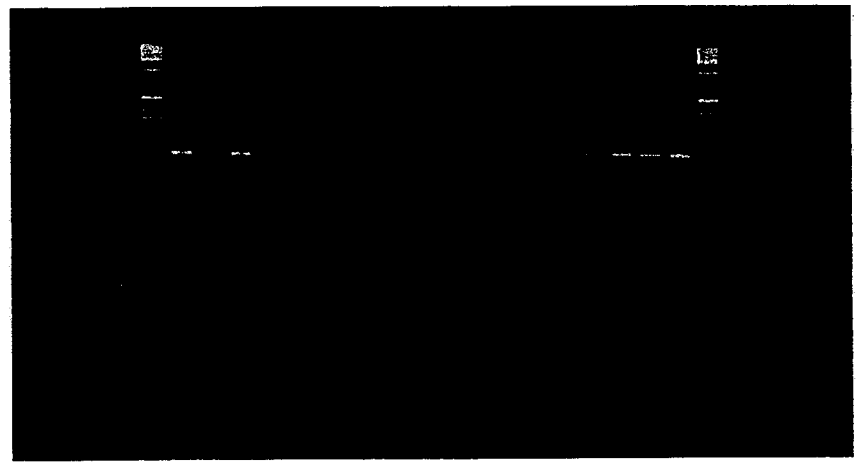
FIG. 4 is a gel photograph showing results of amplification of apc (exon 15) DNA isolated from stool using forward and reverse primers spaced about 200 bp apart. The band intensity relates to the amount of 200 bp product or greater in the sample. Lanes 1–4 are results from patients with cancer or adenoma, lane 5 is a positive control, lanes 6–10 are from patients who did not have cancer or adenoma, lanes 11–12 are negative controls, and lanes 13–18 are standards at the approximate molecular weight indicated in the figure.
Figure 5:
FIG. 5 is a gel photograph showing results of amplification of apc (exon 15) DNA isolated from stool using forward and reverse primers spaced about 200 bp apart. The band intensity relates to the amount of 200 bp product or greater in the sample. Lanes 1–4 are results from patients with cancer or adenoma, lane 5 is a positive control, lanes 6–10 are from patients who did not have cancer or adenoma, lanes 11–12 are negative controls, and lanes 13–18 are standards at the approximate molecular weight indicated in the figure.
Figure 6:
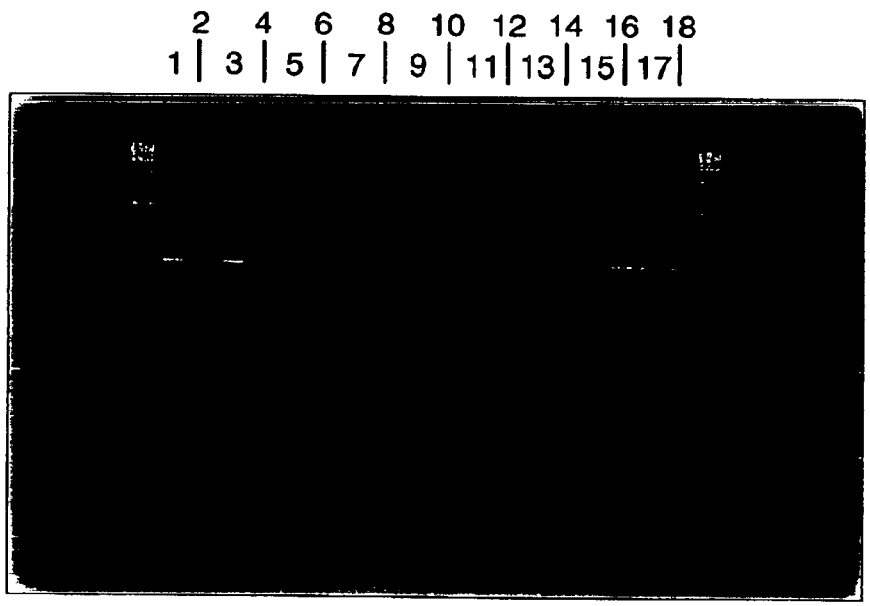
FIG. 6 is a gel photograph showing results of amplification of p53 (exon 5) DNA isolated from stool using forward and reverse primers spaced about 200 bp apart. The band intensity relates to the amount of 200 bp product or greater in the sample. Lanes 1–4 are results from patients with cancer or adenoma, lane 5 is a positive control, lanes 6–10 are from patients who did not have cancer or adenoma, lanes 11–12 are negative controls, and lanes 13–18 are standards at the approximate molecular weight indicated in the figure.
Figure 7:
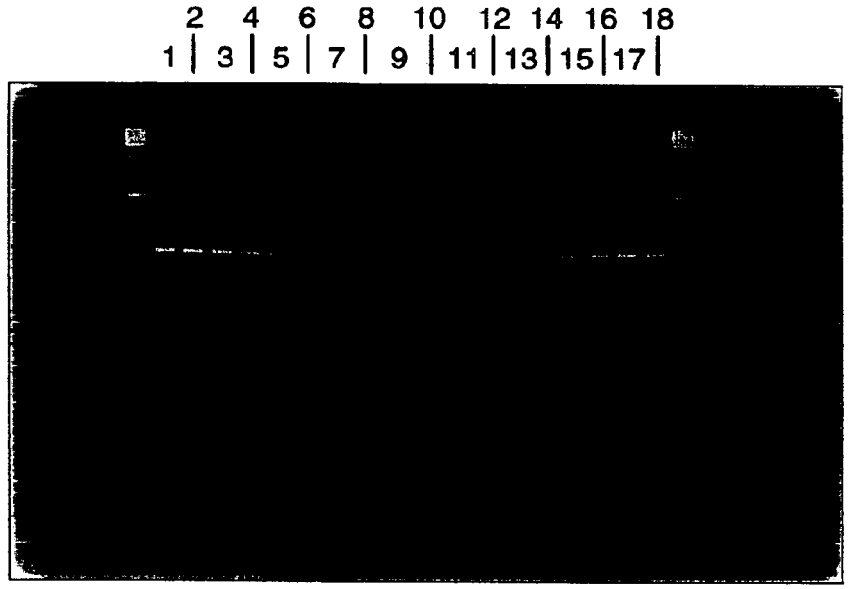
FIG. 7 is a gel photograph showing results of amplification of p53 (exon 7) 25 DNA isolated from stool using forward and reverse primers spaced about 200 bp apart. The band intensity relates to the amount of 200 bp product or greater in the sample. Lanes 1–4 are results from patients with cancer or adenoma, lane 5 is a positive control, lanes 6–10 are from patients who did not have cancer or adenoma, lanes 11–12 are negative controls, and lanes 13–18 are standards at the approximate molecular weight indicated in the figure.
Figure 8:
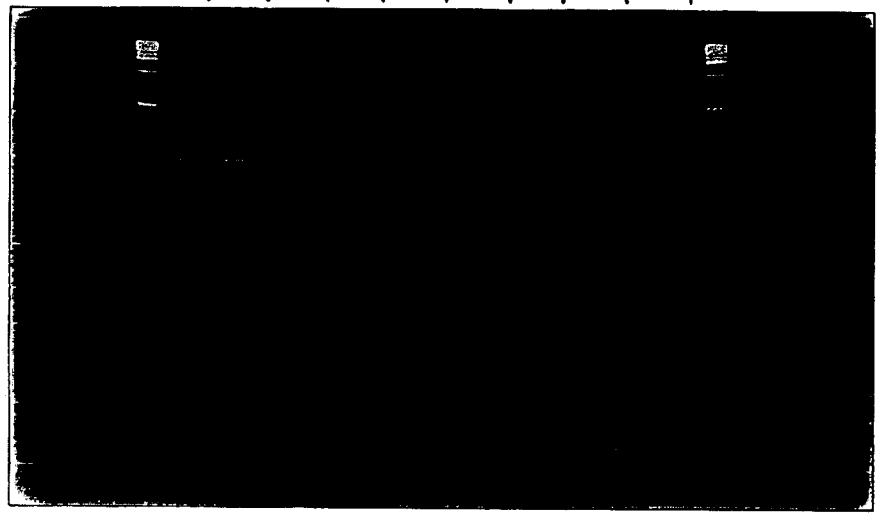
FIG. 8 is a gel photograph showing results of amplification of p53 (exon 8) DNA isolated from stool using forward and reverse primers spaced about 200 bp apart. The band intensity relates to the amount of 200 bp product or greater in the sample. Lanes 1–4 are results from patients with cancer or adenoma, lane 5 is a positive control, lanes 6–10 are from patients who did not have cancer or adenoma, lanes 11–12 are negative controls, and lanes 13–18 are standards at the approximate molecular weight indicated in the figure.

Methods of the invention are based upon the observation that samples comprising cells from patients with cancer or precancer contain a greater amount of high molecular weight (long sequence) DNA fragments as compared to corresponding samples obtained from individuals that are free of cancer/precancer. Accordingly, methods of the invention provide accurate screening and diagnostic procedures for cancer or precancer.

Methods of the invention are useful to detect nucleic acid indicia of cancer or precancer in any tissue or body fluid sample. For example, sputum samples are used to detect the presence of high molecular weight (long sequence) DNA as a marker for cancer. The majority of cells exfoliated into sputum have undergone apoptosis and subsequent further enzymatic degradation. The predominant DNA from those cells is small, apoptotic DNA. Cancer cells produced by, for example, the lungs, the nasal passages, or the trachea will also be sloughed into sputum. However, the DNA from those cells, while being exposed to enzymatic processes, has not been affected by apoptosis. Accordingly, fragments from cancer or precancer cells found in sputum are larger than fragments expected to be produced by normal cells.

Similarly, cells sloughed by cancerous or precancerous lesions in the bladder or kidney produce non-apoptotic DNA in urine, cancerous or precancerous lesions in the lymph nodes result in non-apoptotic DNA fragments in lymph, and cancerous or precancerous cells in the breast slough non-apoptotic DNA-containing cells that can be harvested via aspiration. Accordingly, methods of the invention are useful in any tissue or body fluid. However, for purposes of exemplification of the methods described herein, stool sample were used to predict the presence of colorectal cancer or precancer. Stool Is an excellent specimen for analysis due to the characteristic exfoliation of colonic epithelia as described above.

Methods of the invention are practiced by detecting the presence of DNA fragments having a sequence length that would not be expected to be present in significant amounts in a sample obtained from a healthy individual (i.e., an individual who does not have cancer or precancer). A threshold amount of large fragments is an amount that exceeds a predetermined level expected or determined for non-cancerous/non-precancerous cells. The predetermined level or standard can be determined by detecting the amount of a particular size of DNA fragment (preferably apoptotic fragments characteristic of normal cells) in a population or subpopulation of normal patients. Standards can be determined empirically, and, once determined, can be used as the basis for further screening.

The size of fragments to be used is chosen based upon the convenience of the individual performing the screen. Factors affecting the size of fragments used in screening or diagnostic methods of the invention Include the availability and costs of probes and primers, the desired target of amplification, the type of cancer being screened, and the patient sample on which screening takes place. The invention takes advantage of the recognition that large fragments exist in greater abundance in abnormal samples than in normal samples. Accordingly, the precise size of fragments used in methods of the invention does not matter. For any given size of fragments to be analyzed, a cutoff must be determined to distinguish between normal and abnormal samples. Preferably, the cutoff is determined empirically based upon known normal and abnormal sample, and then is used in future screenings.

The following examples provide further details of methods according to the invention. For purposes of exemplification, the following examples provide details of the use of the method if the present invention in colon cancer detection. Accordingly, while exemplified in the following manner, the invention is not so limited and the skilled artisan will appreciate its wide range of application upon consideration thereof.

Exemplary Method for the Detection of Colon Cancer

For the analysis of stool samples, preferred methods of the invention comprise obtaining at least a cross-section or circumfrential portion of a voided stool as taught in U.S. Pat. No. 5,741,650, and co-pending, co-owned U.S. patent application Ser. No. 09/059,718, both of which are incorporated by reference herein. While a cross-sectional or circumfrential portion of stool is desirable, methods provided herein are conducted on random samples obtained from voided stool, which include smears or scrapings. Once obtained, the stool specimen Is homogenized. A preferable buffer for homogenization is one that contains at least 16 mM ethylenediaminetetraacetic acid (EDTA). However, as taught in co-pending, co-owned U.S. patent application Ser. No. 60/1122,177, incorporated by reference herein, it has been discovered that the use of at least 150 mM EDTA greatly improves the yield of nucleic acid from stool. Thus, a preferred buffer for stool homogenization comprises phosphate buffered saline, 20–100 mM NaCl or KCl, at least 150 mM EDTA, and optionally a detergent (such as SDS) and a proteinase (e.g., proteinase K).

After homogenization, nucleic acid is preferably isolated from the stool sample. Isolation or extraction of nucleic acid is not required in all methods of the invention, as certain detection techniques can be adequately performed in homogenized stool without isolation of nucleic acids. In a preferred embodiment, however, homogenized stool is spun to create a supernatant containing nucleic acids, proteins, lipids, and other cellular debris. The supernatant is treated with a detergent and proteinase to degrade protein, and the nucleic acid is phenol-chloroform extracted. The extracted nucleic acids are then precipitated with alcohol. Other techniques can be used to isolate nucleic acid from the sample. Such techniques include hybrid capture, and amplification directly from the homogenized stool. Nucleic acids can be purified and/or isolated to the extent required by the screening assay to be employed. Total DNA is isolated using techniques known in the art.

Once DNA is isolated, the sample preferably is enriched for human nucleic acids using sequence specific capture probes. Pelletized DNA is resuspended in TE buffer. Guanidine isothiocyanatate (GITC) is then added. An excess of capture probes that target human DNA are added to the sample. The sample is heated to denature the DNA and then cooled. Finally, probe and target DNA are allowed to hybridize. Steptavidin -coated magnetized beads are suspended in water and added to the mixture. After briefly mixing, the mixture is maintained at room temperature for approximately 30 minutes. Once the affinity binding is completed, a magnetic filed is applied to the sample to draw the magnetized isolation beads (both with and without hybridized complex). The beads are then washed four (4) times in 1M GITCl 0.1% Igepal (Sigma, St. Louis, Mo.) solution for 15 minutes, followed by two (2) washes with warm buffer (TE with 1M NaCl) for 15 minutes in order to isolate complexed streptavidin. Finally, distilled water is added to the beads and heated to elude the DNA. Gel electrophoresis can then be performed on the human DNA that has been captured.

III. Determination of Fragment Length

The size of human DNA fragments obtained above can be determined by numerous means. For example, human DNA can be separated using gel electrophoresis. A 5% acrylamide gel is prepared using techniques known in the art. See Ausubel et. al., Short Protocols in Molecular Biology, John Wiley & Sones, 1195, pgs. 2-23–2-24, incorporated by reference herein. The size of human DNA fragments is then determined by comparison to known standards. Fragments greater than about 200 bp provide a positive screen. While a diagnosis can be made on the basis of the screen alone, patients presenting a positive screen are preferably advised to seek follow-up testing to render a confirmed diagnosis.

A preferred means for determining human DNA fragment length is by using PCR. Methods for implementing PCR are well-known. In the present invention, human DNA fragments are amplified using human-specific primers. Amplicon of greater than about 200 bp produced by PCR represents a positive screen. Other amplification reactions and modifications of PCR, such as ligase chain reaction, reverse-phase PCR, Q-PCR, and others may be used to produce detectable levels of amplicon. Amplicon may be detected by coupling to a reporter (e.g. flouresence, radioisotopes, and the like), by sequencing, by gel electrophoresis, by mass spectrometry, or by any other means known in the art, as long as the length, weight, or other characteristic of the amplicons identifies them by size.

EXAMPLES

Experiments were conducted to determine whether characteristics of amplifiable DNA in stool were predictive of cancer or precancer in patients from whom stools samples were obtained. In the first experiment, the amount of amplifiable DNA was measured in each of several stool samples using PCR amplification to detect DNA fragments in the sample of at least 200 base pairs in length. The second experiment determined the amount of long (greater than 200 base pair) fragments in the same samples, and then to determine ratios of long product to short product.

I. The Use of Amplifiable DNA as a Marker for Cancer or Precancer

Stool samples were collected from 9 patients who presented with symptoms or a medical history that indicated that a colonoscopy should be performed. Each stool sample was frozen. Immediately after providing a stool sample, each patient was given a colonoscopy in order to determine the patient's disease status. Based upon the colonoscopy results, and subsequent histological analysis of biopsy samples taken during colonsocopy, individuals were placed into one of two groups: normal or abnormal. The abnormal group consisted of patients with cancer or with an adenoma of at least 1 cm in diameter. Based upon these results, 4 of the 9 patients were placed into the abnormal group.

The samples were screened by hybrid capturing human DNA, and determining the amount of amplifiable DNA having at least 200 base pairs. Each frozen stool specimen, weighing from 7–33 grams, was though and homogenized in 500 mM Tris, 16 mM EDTA, and 10 mM NaCl, pH 9.0 at a volume: to mass ratio of 3:1. Samples were then rehomogenized in the same buffer to a final volume-to-mass ratio of 20:1, and spun in glass macro beads at 2356×g. The supernatant was collected and treated with SDS and proteinase k. The DNA was then phenol-chloroform extracted and precipitated with alcohol. The precipitate was suspended In 10 mM Tris and 1 mM EDTA.(1×TE), pH 7.4. Finally, the DNA was treated with Rnase.

Human DNA was isolated from the precipitate by sequence-specific hybrid capture. Biotynilated probes against portions of the p53, K-ras, and apc genes were used. The K-ras probe was 5'GTGGAGTATTTGATAGTGTAT-TAACCTTATGTGTGAC 3' (SEQ ID NO: 1). There were two apc probes: apc-1309 was 5'TTCCAGCAGTGTCA-CAGCACCCTAGAACCAAATCCAG 3' (SEQ ID NO: 2), and apc-1378 was 5'CAGATAGCCCTGGACAAACAAT-GCCACGAAGCAGAAG 3' (SEQ ID NO: 3). There were four probes against p53, the first (hybridizing to a portion of exon 5) was 5'TACTCCCCTGCCCTCAACAAGAT-GTTTTGCCAACTGG3' (SEQ ID NO:4), the second (hybridizing to a portion of exon 7) was 5'ATTTCTTCCAT-ACTACTACCCATCGACCTCTCATC3' (SEQ ID NO: 5), the third, also hybridizing to a portion of exon 7 was 5'ATGAGGCCAGTGCGCCTTGGGGAGACCT-GTGGCAAGC3' (SEQ ID NO: 6); and finally, a probe against exon 8 had the sequence 5'GAAAGGA-CAAGGGTGGTTGGGAGTAGATGGAGCCTGG3' (SEQ ID NO: 7). A 10 ul aliquot of each probe (20 pmol/capture) was added to a suspension containing 300 ul DNA in the presence of 310 ul 6M GITC buffer for 2 hours at room temperature. Hybrid complexes were isolated using streptavidin-coated beads (Dynal). After washing, probe-bead complexes were suspended at 25° C. for 1 hour in 0.1×TE buffer, pH7.4. The suspension was then heated for 4 minutes at 85° C., and the beads were removed.

Captured DNA was then amplified using PCR, essentially as described in U.S. Pat. No. 4,683,202, incorporated by reference herein. Each sample was amplified using forward and reverse primers through 7 loci (Kras, exon 1, APC exon 15 (3 separate loci), p53, exon 5, p53, exon 7, and p53, exon 8) in duplicate (for a total of 14 amplifications for each locus). Seven separate PCRs (33 cycles each) were run in duplicate using primers directed to detect fragments in the sample having 200 base pairs or more. Amplified DNA was placed on a 4% Nusieve (FMC Biochemical) gel (3% Nusieve, 1% agarose), and stained with ethidium bromide (0.5 ug/ml). The resulting amplified DNA was graded based upon the relative intensity of the stained gels. The results are shown in FIGS. 2–8. Each Figure represents the results for all 9 patients (including standards) for the seven different loci that were amplified. As shown in the Figures, each sample from a patient with cancer or adenoma was detected as a band having significantly greater intensity than the bands associated with samples from patients who did not have cancer or precancer. All four cancer/adenoma patients identified using colonoscopy were correctly identified by determining the amount of amplifiable DNA 200 base pairs or greater in length. As shown in FIGS. 2–8, the results were the same regardless of which locus was amplified. Accordingly, the amount of 200 bp or greater DNA in a sample was predictive of patient disease status.

EXAMPLE 2

An experiment was conducted that was essentially identical to the one described above in Example 1, but forward and reverse primers were placed such that fragments of about 1.8 Kb and above were amplified.

Figure 9:
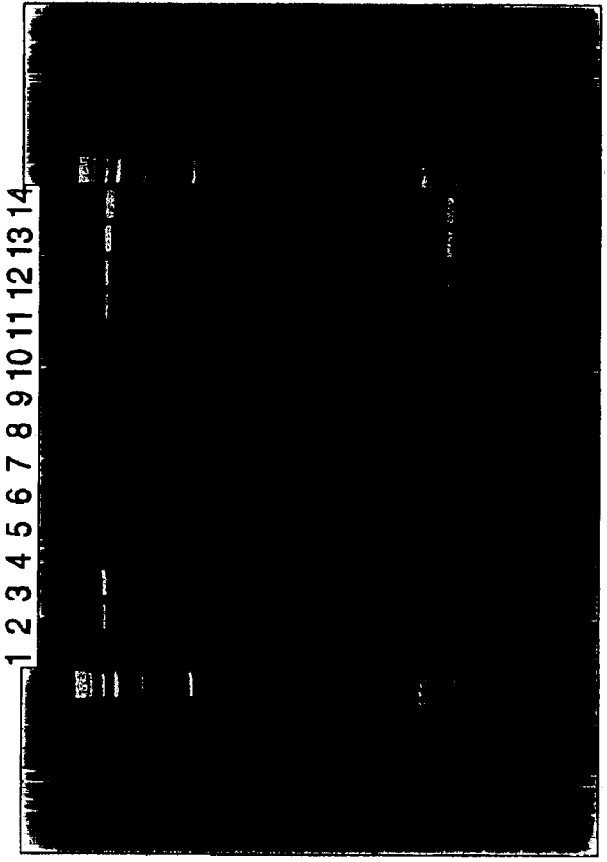
FIG. 9 is a gel photograph of results of amplification of DNA from stool samples using forward and reverse primers spaced approximately 1.8 Kb apart. The band intensity shows the amount of 1.8 Kb or greater product. Lanes 1, 8, and 9 are negative controls, lanes 2, 3 , and 5 are results from patients with cancer or adenoma, lanes 4, 6 , and 7 are results from patients who did not have cancer or adenoma, and lanes 10–14 are molecular weight standards.
Figure 10:
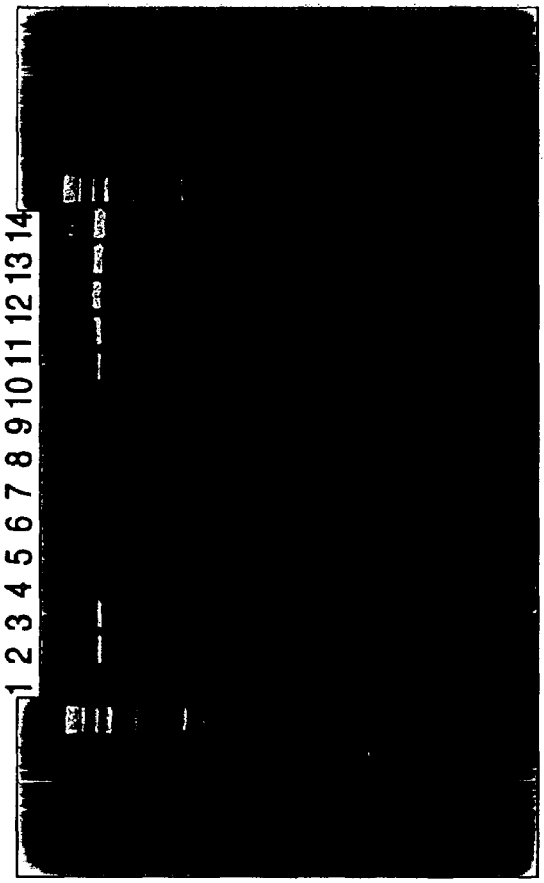
FIG. 10 is a gel photograph of results of amplification of DNA from stool samples using forward and reverse primers spaced approximately 1.8 Kb apart. The band intensity shows the amount of 1.8 Kb or greater product. Lanes 1, 8 , and 9 are negative controls, lanes 2, 3, and 5 are results from patients with cancer or adenoma, lanes 4, 6, and 7 are results from patients who did not have cancer or adenoma, and lanes 10–14 are molecular weight standards.
Figure 11:
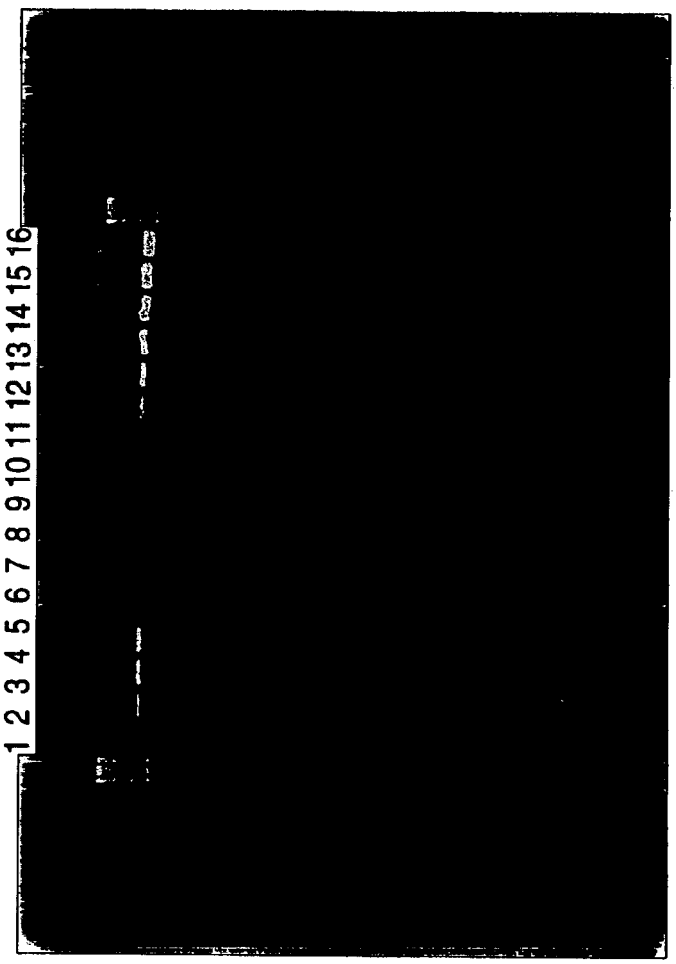
FIG. 11 is a gel photograph of results of amplification of DNA from stool samples using forward and reverse primers spaced approximately 1.8 Kb apart. The band Intensity shows the amount of 1.8 Kb or greater product. Lanes 1, 8, and 9 are negative controls, lanes 2, 3, and 5 are results from patients with cancer or adenoma, lanes 4, 6, and 7 are results from patients who did not have cancer or adenoma, and lanes 10–14 are molecular weight standards.

DNA was prepared as described above. Forward and reverse primers were spaced so as to hybridize approximately 1.8 Kb apart on three different loci (Kras, exon 1, APC, exon 15, and p53 exon 5). Thirty-three rounds of amplification were performed, and the resulting DNA was placed on a 5% acrylamide gel. The results are shown in FIGS. 9–11. As shown in the Figures (which show results from three separate experiments to amplify and detect "long" product), samples from individuals having cancer or precancer produced large amounts of high-molecular weight (in this case 1.8 Kb and above) DNA; whereas samples from patients who did not have cancer or precancer produced no DNA In the range of about 1.8 Kb and higher. Thus, the presence of high-molecular weight DNA was indicative of the disease status of the patient.

The invention has been described in terms of its preferred embodiments. Alternative embodiments are apparent to the skilled artisan upon examination of the specification and claims.

What is claimed is:

1. A method for screening a patient for a colorectal cancer or a colorectal precancer, the method comprising the steps of:

detecting in a patient stool sample comprising exfoliated cells or cellular debris a first amount of a long nucleic acid of a length greater than 200 base pairs in length; wherein said long nucleic acid is present in both normal and cancerous or precancerous cells;

comparing the first amount of long nucleic acid in said patient stool sample to a second amount of said long nucleic acid present in a stool sample from patient free of colorectal cancer or precancer;

determining whether said first amount of long nucleic acid exceeds the second amount of long nucleic acid in said sample from a patient free of colorectal cancer or precancer; and;

identifying a positive screen for an indicator of a colorectal cancer or precancer if said amount of long nucleic acid in said patient stool sample does exceed said second amount of long nucleic acid in said sample from a patient free of colorectal cancer or precancer.

2. The method for screening a patient for a colorectal cancer or a colorectal precancer, the method comprising the steps of:

determining in patient stool sample comprising exfoliated cells or cellular debris a first amount of long nucleic acid of a length greater then 200 base pairs;

determining in said stool sample a second amount of nucleic acid of a length less than said long nucleic acid;

determining a ratio between said first amount and said amount; and identifying a positive screen for an indicator of a colorectal cancer or precancer if said ratio exceeds a threshold ratio for patient who do not have a colorectal cancer or a precancer.

3. The method of claim 1 or claim 2, wherein said detecting or determining comprises conducting an amplification reaction designed to amplify only nucleic acids fragments that are greater than 200 base pair in length.

4. The method of claim 1 or claim 2, further comprising the step of enriching said sample for human DNA.

5. The method of claim 1 or claim 2, further comprising the step of isolating human DNA from said sample.

* * * * *

UNITED STATES PATENT AND TRADEMARK OFFICE
CERTIFICATE OF CORRECTION

PATENT NO. : 6,964,846 B1
APPLICATION NO. : 09/545162
DATED : November 15, 2005
INVENTOR(S) : Anthony P. Shuber It is certified that error appears in the above-identified patent and that said Letters Patent is hereby corrected as shown below:

In Claim 2, column 14, line 32, replace "then" with --than--.

In Claim 2, column 14, line 35, insert --second-- after the phrase "determining a ratio between said first amount and said".

Signed and Sealed this

Twelfth Day of August, 2008

JON W. DUDAS
*Director of the United States Patent and Trademark Office*